United States Patent
Farnan et al.

(10) Patent No.: US 10,350,384 B2
(45) Date of Patent: Jul. 16, 2019

(54) TWO-PIECE TRANSSEPTAL CANNULA, DELIVERY SYSTEM, AND METHOD OF DELIVERY

(71) Applicant: CircuLite, Inc., Teaneck, NJ (US)

(72) Inventors: Robert C. Farnan, Ridgewood, NJ (US); Scott A. Olson, Zimmerman, MN (US); Elizabeth Jung, Zimmerman, MN (US); Andrew J. Dusbabek, Dayton, MN (US); Robert G. Hudgins, Monticello, MN (US)

(73) Assignee: CircuLite, Inc., Teaneck, NJ (US)

( * ) Notice: Subject to any disclaimer, the term of this patent is extended or adjusted under 35 U.S.C. 154(b) by 708 days.

(21) Appl. No.: 14/191,792

(22) Filed: Feb. 27, 2014

(65) Prior Publication Data

US 2014/0200550 A1    Jul. 17, 2014

Related U.S. Application Data

(63) Continuation of application No. 12/720,039, filed on Mar. 9, 2010, now abandoned.

(Continued)

(51) Int. Cl.
| | |
|---|---|
| A61M 1/10 | (2006.01) |
| A61M 25/00 | (2006.01) |
| A61M 1/36 | (2006.01) |
| A61M 25/04 | (2006.01) |
| A61M 29/00 | (2006.01) |
| A61M 1/12 | (2006.01) |
| A61B 17/34 | (2006.01) |
| A61M 25/02 | (2006.01) |

(52) U.S. Cl.
CPC ..... *A61M 25/0068* (2013.01); *A61B 17/3478* (2013.01); *A61M 1/1008* (2014.02);
(Continued)

(58) Field of Classification Search
CPC ... A61M 1/122; A61M 1/3653; A61M 1/3659
See application file for complete search history.

(56) References Cited

U.S. PATENT DOCUMENTS 5,478,309 A * 12/1995 Sweezer et al. ............. 604/6.14
5,904,703 A     5/1999 Gilson
(Continued)

FOREIGN PATENT DOCUMENTS

JP    2004536625 A    12/2004
WO    02074174 A2     9/2002

OTHER PUBLICATIONS

Japanese Patent Office, Office Action in JP Application No. 201499372, dated Mar. 23, 2015.

(Continued)

*Primary Examiner* — Joseph M Dietrich
(74) *Attorney, Agent, or Firm* — Christopher & Weisberg, P.A.

(57) ABSTRACT

A cannula assembly for directing blood from the heart of a patient and a minimally invasive method of implanting the same. The cannula assembly includes a flexible cannula body having a proximal end and a distal end with a receiving portion, and a transseptal tip having a distal end and a proximal end with an engaging portion. First and second anchors are coupled to the transseptal tip and configured to be deployed from a contracted state to an expanded state. The engaging portion of the transseptal tip is operable to removably engage the receiving portion of the flexible cannula body in vivo.

17 Claims, 34 Drawing Sheets

Related U.S. Application Data

(60) Provisional application No. 61/163,931, filed on Mar. 27, 2009.

(52) U.S. Cl.
CPC .......... *A61M 1/122* (2014.02); *A61M 1/3653* (2013.01); *A61M 1/3659* (2014.02); *A61M 25/005* (2013.01); *A61M 25/04* (2013.01); *A61M 29/00* (2013.01); *A61M 1/12* (2013.01); *A61M 2025/0233* (2013.01); *A61M 2205/0266* (2013.01)

(56) References Cited

U.S. PATENT DOCUMENTS

| | | | | |
|---|---|---|---|---|
| 6,406,420 | B1* | 6/2002 | McCarthy et al. | 600/16 |
| 2002/0077555 | A1* | 6/2002 | Schwartz | A61B 5/0031 600/486 |
| 2004/0024435 | A1* | 2/2004 | Leckrone et al. | 607/101 |
| 2005/0033396 | A1* | 2/2005 | Ospyka | 607/130 |
| 2008/0109069 | A1 | 5/2008 | Coleman et al. | |
| 2010/0004501 | A1* | 1/2010 | Whisenant et al. | 600/16 |

OTHER PUBLICATIONS

Japanese Patent Office, Office Action in Serial No. JP201499373, dated Mar. 16, 2015.
European Patent Office, Official Action in EP Application No. EP10250524.5, dated Jul. 7, 2015.
Japanese Patent Office, Decision of Rejection in JP Application No. 2014-099373, dated Nov. 16, 2015.
Canadian Intellectual Property Office, Office Action in Canadian Application No. 2,697,389, dated Jan. 22, 2016.
Japanese Patent Office, Notice of Reasons for Rejection in JP Application No. 201499372, dated Jul. 25, 2016.
Japanese Patent Office, Decision of Rejection in JP Application No. 2014-099373, dated Dec. 26, 2016.

* cited by examiner

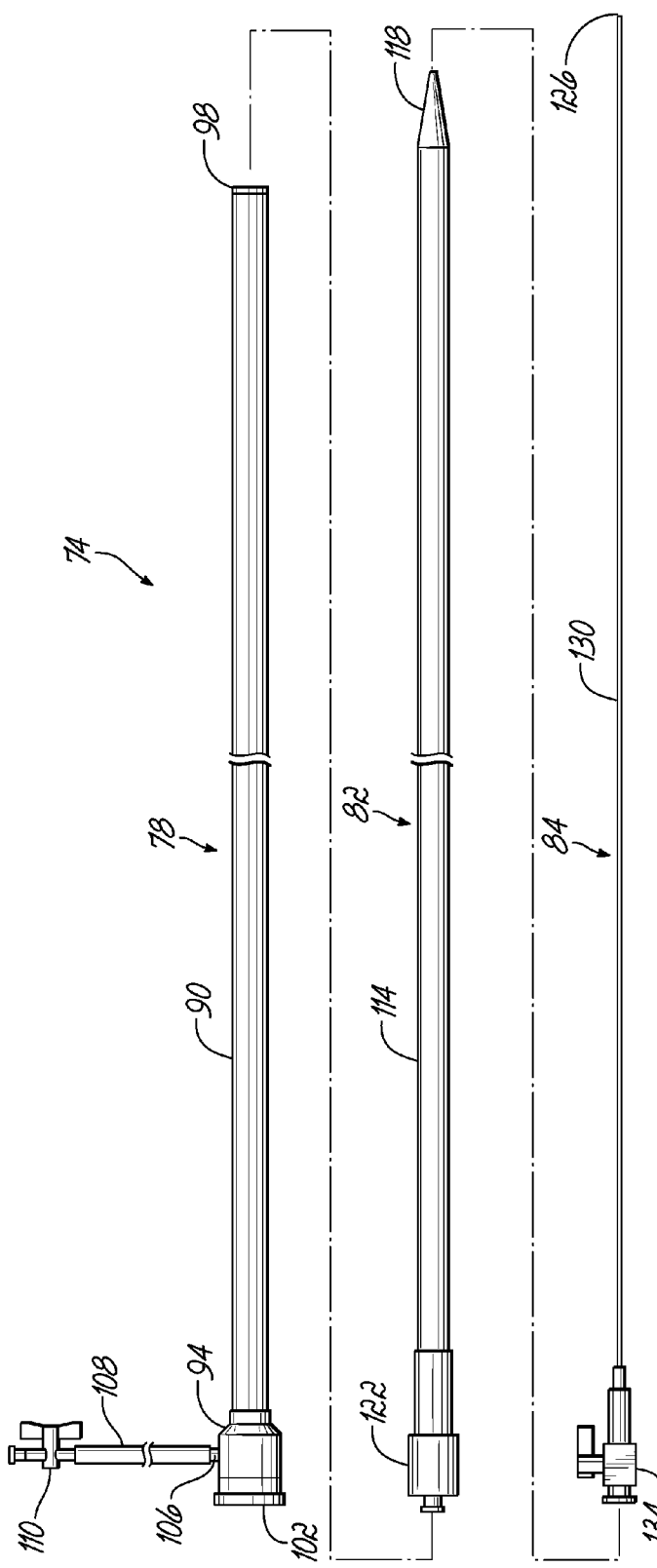
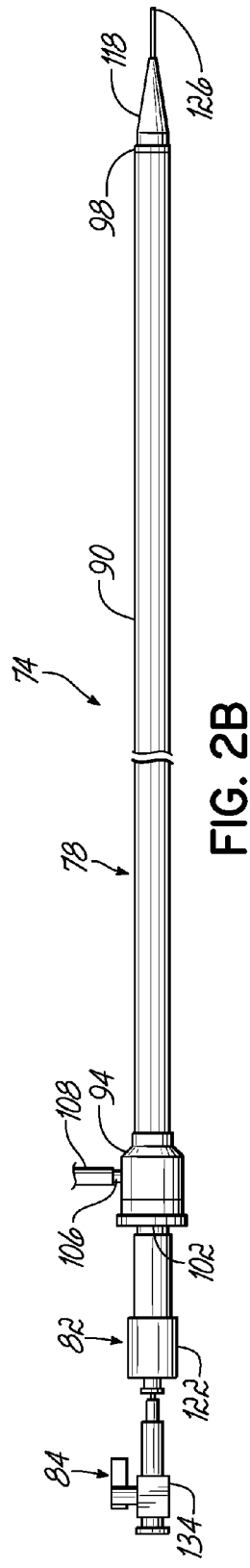
FIG. 2A
FIG. 2B

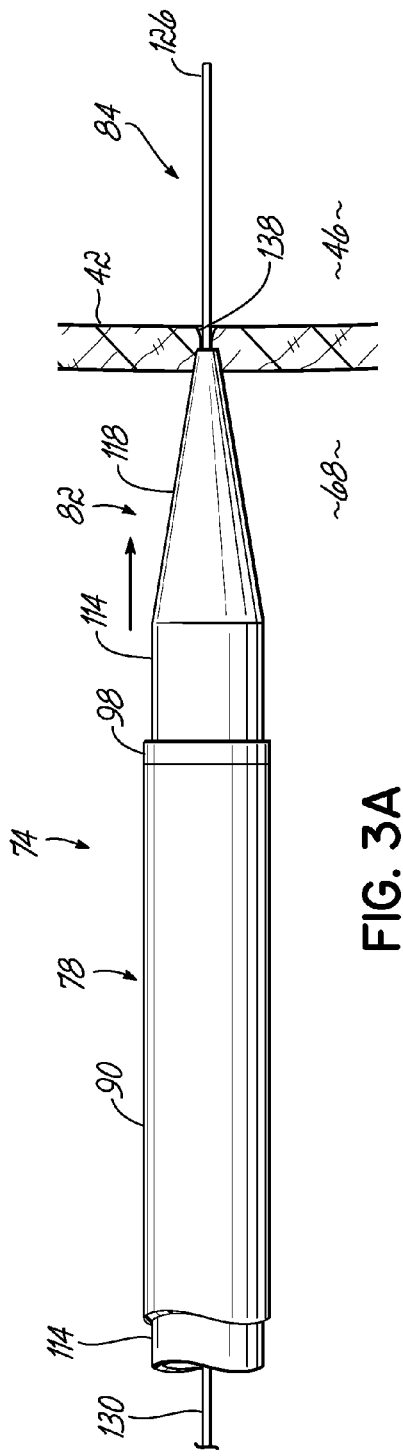
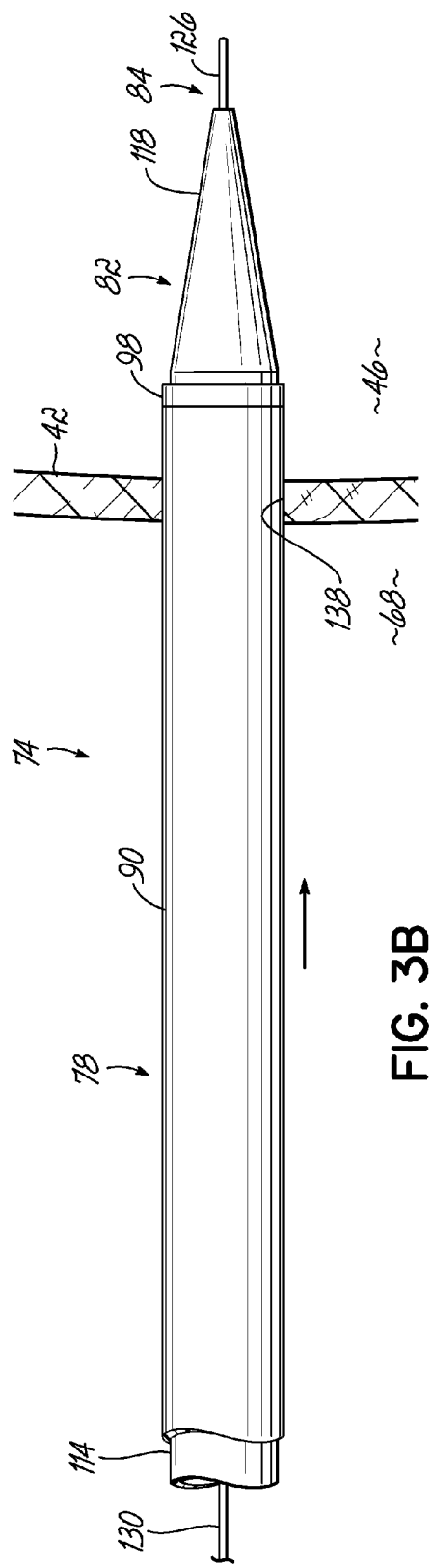

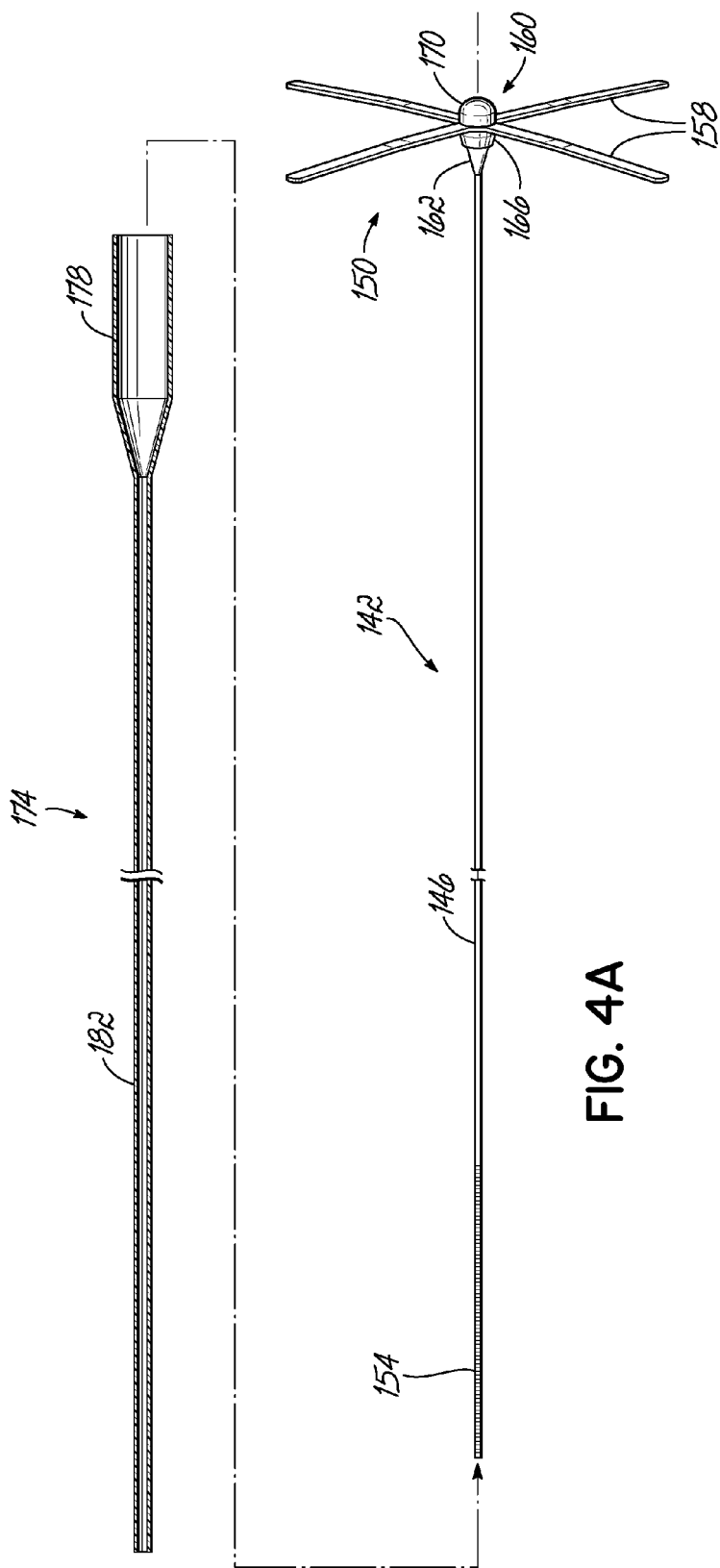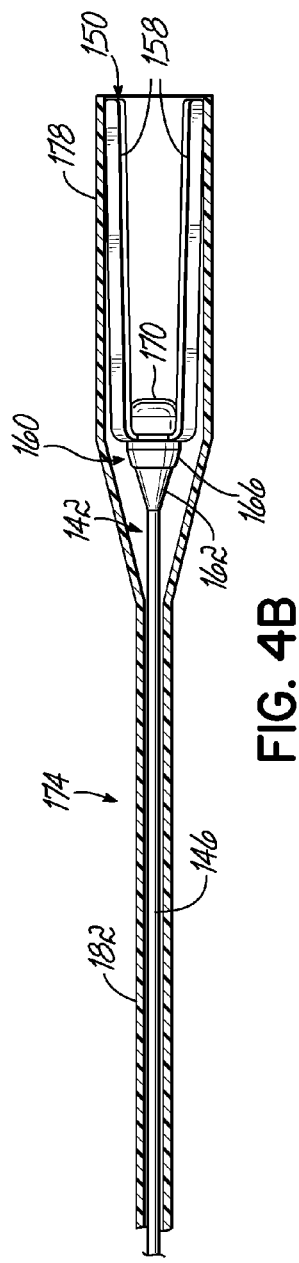
FIG. 4A
FIG. 4B

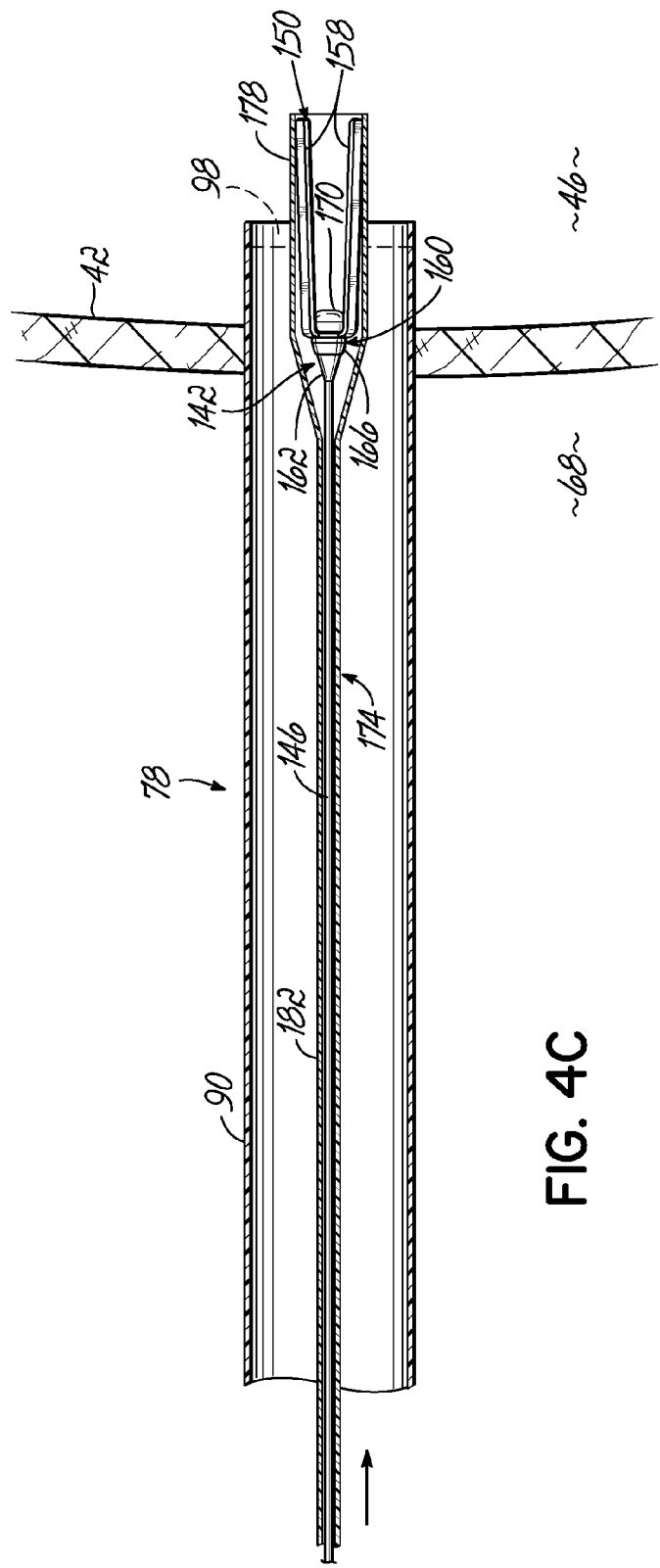

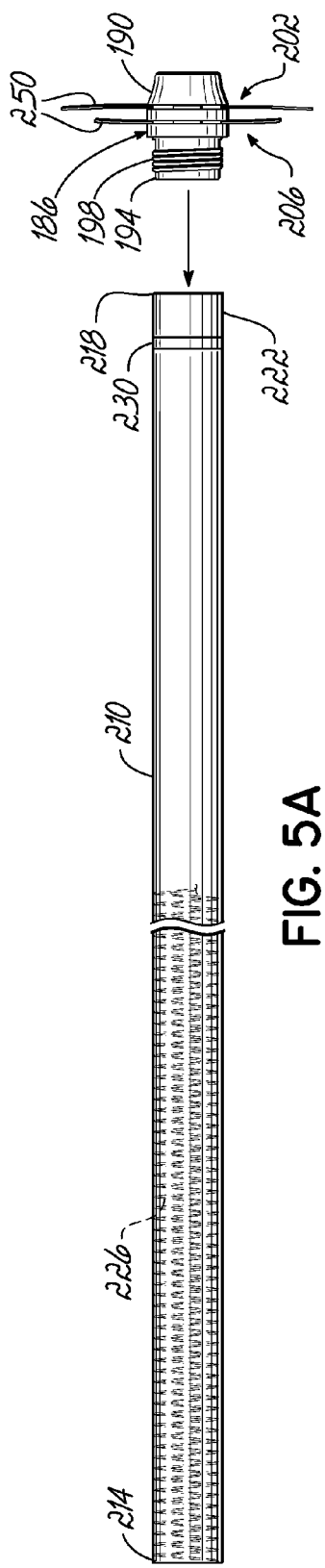
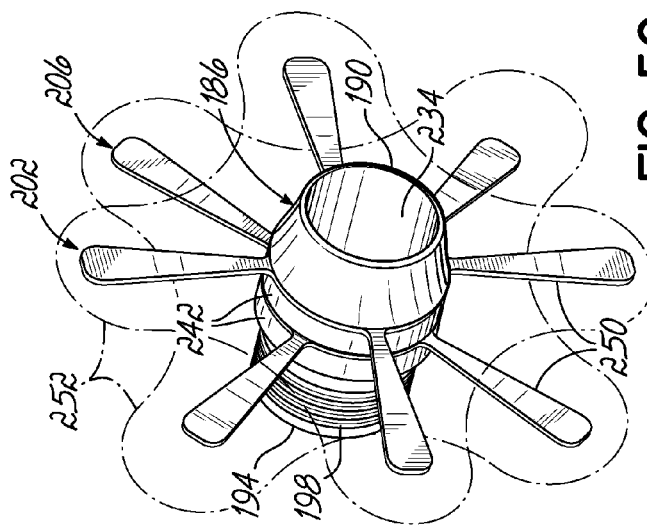
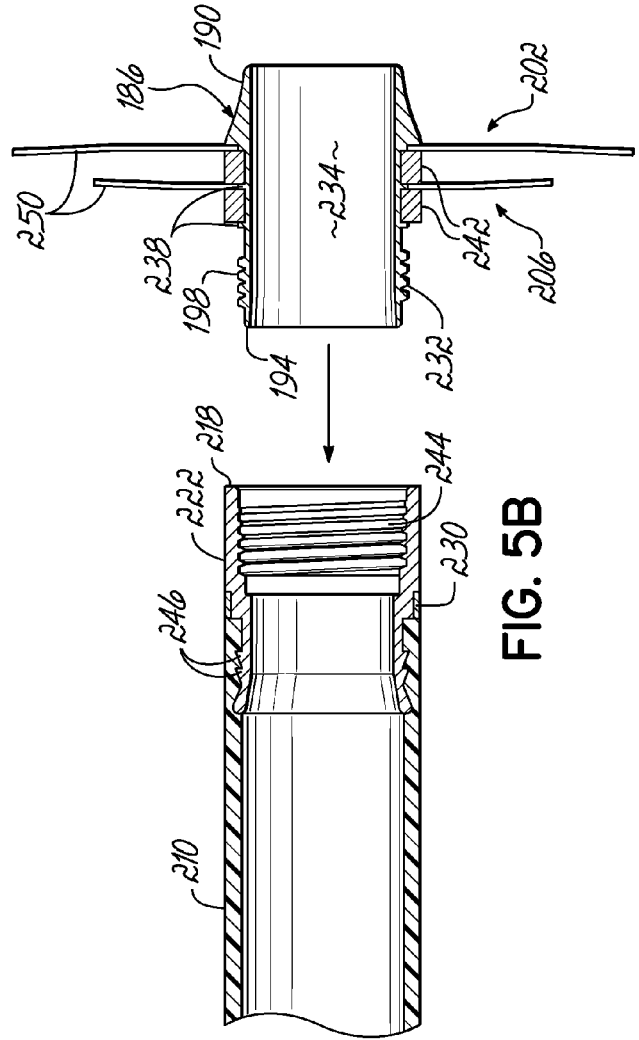

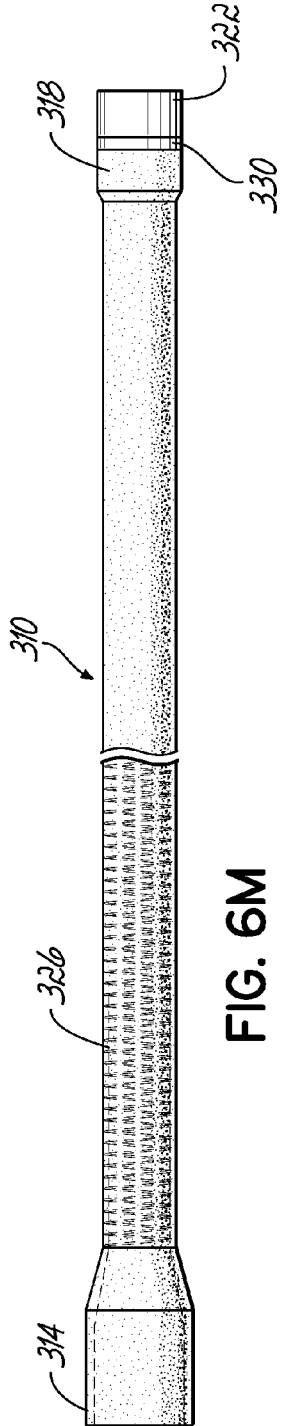
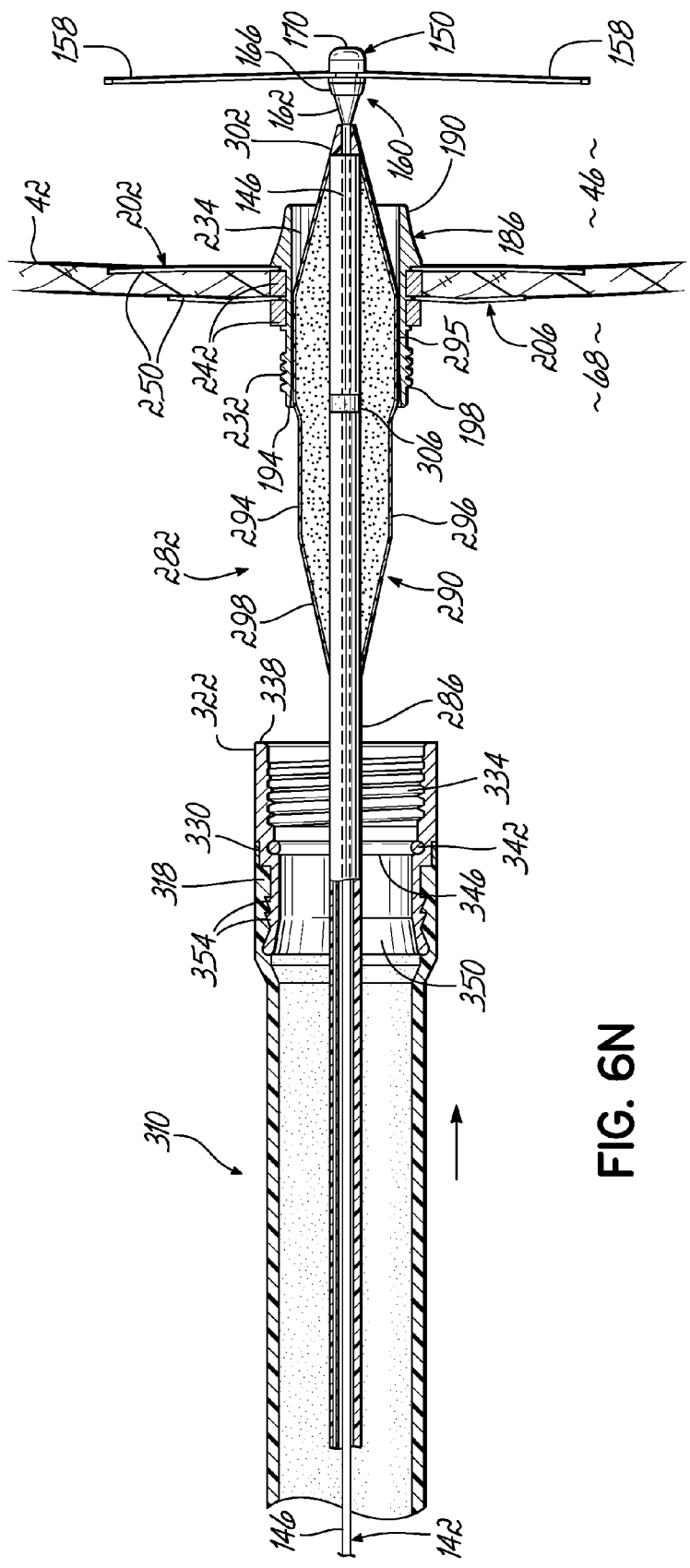
FIG. 6M
FIG. 6N

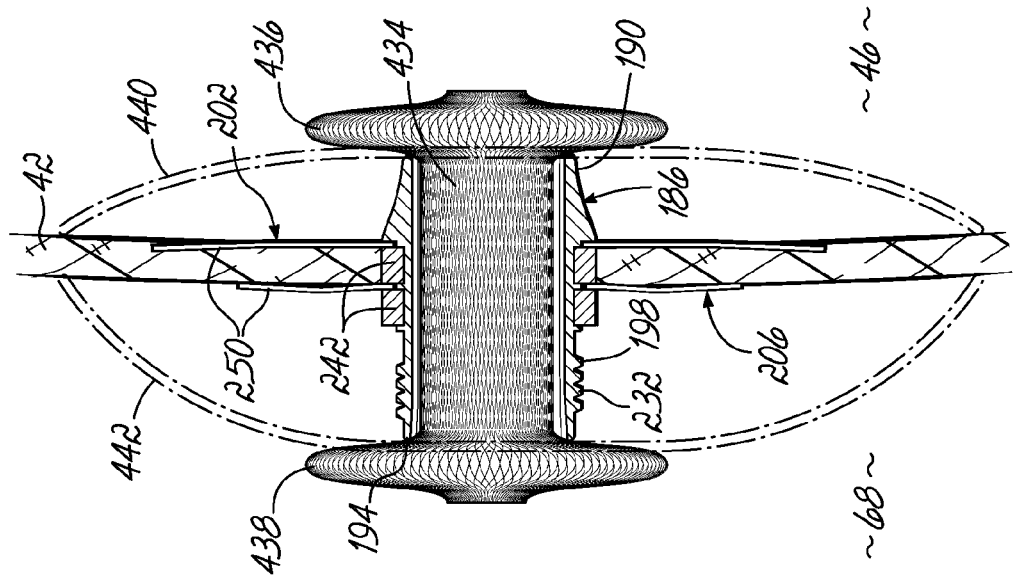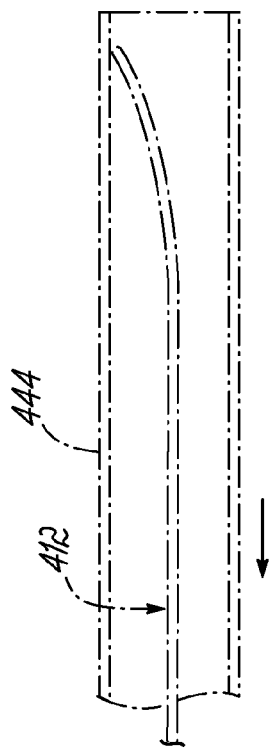
FIG. 7F

TWO-PIECE TRANSSEPTAL CANNULA, DELIVERY SYSTEM, AND METHOD OF DELIVERY

CROSS-REFERENCE TO RELATED APPLICATIONS

This application is a continuation of U.S. application Ser. No. 12/720,039, filed Mar. 9, 2010 (pending) which claims the priority of U.S. Provisional Patent Application Ser. No. 61/163,931, filed on Mar. 27, 2009, the disclosures of which are incorporated by reference herein.

TECHNICAL FIELD

The present invention generally relates to a method of implanting a circulatory assist system, and more particularly, to the method of implanting a cannula assembly of the circulatory assist system.

BACKGROUND

The human heart is the muscle that is responsible for pumping blood throughout the vascular network. Veins are vessels that carry blood toward the heart while arteries are vessels that carry blood away from the heart. The human heart consists of two atrial chambers and two ventricular chambers. Atrial chambers receive blood from the body and the ventricular chambers, which include larger muscular walls, pump the blood from the heart. A septum separates the left and the right sides of the heart. Blood from the veins of the vascular network enters the right atrium from the superior and inferior vena cava and moves into the right ventricle. From the right ventricle, the blood is pumped to the lungs via pulmonary arteries to become oxygenated. Once the blood has been oxygenated, the blood returns via pulmonary veins to the heart by entering the left atrium. From the left atrium, the blood enters the left ventricle and is pumped into the aorta and then into the arteries of the vascular network.

For the vast majority of the population, the events associated with the movement of blood happen without circumstance. However, for many people the heart fails to provide adequate pumping capabilities. These heart failures may include congestive heart failure (commonly referred to as heart disease), which is a condition that results in any structural or functional cardiac disorder. The structural or functional disorder impairs the ability of the heart to fill with or pump blood throughout the body. Presently, there is no known cure for heart disease and long-term treatment is limited to a heart transplant. With only a little over 2,000 patients receiving a heart transplant each year, and over 16,600 more on the waiting list for a heart, there is a persisting need for a cure or at the minimum a means of improving the quality of life of those patients on the waiting list.

One such means of bridging the time gap while awaiting a transplant is a circulatory assist system. Circulatory assist devices were developed over a decade ago and provide assistance to a diseased heart by way of a mechanical pump. In this way, the circulation of blood through the vascular network is aided despite the presence of diseased tissue. Traditionally, these circulatory assist devices include an implantable pump, a controller (internal or external), and inflow and outflow tubes connecting the pump to the vascular network. FDA approved circulatory assist devices may be used to partially relieve symptoms of breathlessness and fatigue associated with severe heart failure and can drastically improve a patient's quality of life.

However, the conventional surgical process associated with the circulatory assist system is highly invasive. At the very least the procedure involves a thoracotomy, i.e., the opening of the thoracic cavity between successive ribs to expose the internal organs. More typical is cardiac surgery, generally known as open-heart surgery, where the sternum is cut and split to expose the internal organs. Once the thoracic cavity is accessed, the physician must enter the pleural space and puncture both the pericardium and the myocardial wall. There are great risks and an extensive recovery time associated with the invasive nature of the implantation surgery. As such, some patients with severe symptoms are not healthy enough for surgery to receive a circulatory assist system.

The transseptal cannula, described in related U.S. patent application Ser. No. 12/256,911, the disclosure of which is incorporated herein by reference, provides greater accessibility to the circulatory assist device to those patients that would receive the most benefit by minimizing the invasiveness of the implantation surgery. Yet, there continues to be a need to implement additional features that would further facilitate the delivery of the transseptal cannula and/or that would allow the physician to maintain greater control over the transseptal cannula device during the surgical procedure.

SUMMARY

In one illustrative embodiment, the present invention is directed to a cannula assembly. The cannula assembly includes a flexible cannula body having distal and proximal ends with a lumen extending therebetween. The distal end of the flexible cannula body includes a receiving portion. A transseptal tip has a distal end and a proximal end with an engaging portion. The engaging portion of the transseptal tip is operable to connect to the receiving portion of the flexible cannula body, in vivo. First and second anchors are coupled to the transseptal tip and are configured to be deployed from a contracted state to an expanded state. The first and second anchors are also configured to engage opposite sides of a heart tissue when in the expanded state.

The first and second anchors can each include a plurality of struts extending generally transverse to a lengthwise central axis of the flexible cannula body. The plurality of struts can be formed from a superelastic material and can be folded to a position that is generally parallel with the lengthwise central axis when in the contracted state.

Another illustrative embodiment of the present invention includes a transseptal tip delivery system in combination with the cannula assembly. The transseptal tip delivery system includes a delivery catheter and a delivery sheath. The delivery catheter has distal and proximal ends and a lumen extending therebetween. The distal end of the delivery catheter includes a receiving portion that is operable to removably disengage the engaging portion of the transseptal tip in vivo. The delivery sheath receives the delivery catheter with the transseptal tip and moves relative thereto. Moving the delivery sheath can deploy the first and second anchors into the expanded state.

Another illustrative embodiment of the present invention includes a cannula guide in combination with the cannula assembly. The cannula guide includes an expandable member having distal and proximal tapers and an alignment section therebetween. A body of the cannula guide extends proximally from the expandable member. The expandable member of the cannula guide is configured to engage an inner surface of the transseptal tip and to resist movement of the transseptal tip from the heart tissue while the flexible cannula body is connected to the engaging portion of the transseptal tip, in vivo.

In another illustrative embodiment of the present invention, a method of implanting the cannula assembly within a heart tissue of a patient is provided. The method includes introducing the transseptal tip to the heart tissue, directing the flexible cannula body to the transseptal tip, and connecting the receiving portion of the flexible cannula body to the engaging portion of the transseptal tip, in vivo.

The method of implanting can include deploying the first and second anchors to engage opposite sides of the heart tissue in the expanded state. The deploying can further include deploying a plurality of struts comprising the first and second anchors from a position generally parallel with a lengthwise central axis of the flexible cannula body to a position generally transverse to the lengthwise central axis.

The method of implanting can further include advancing and deploying an anchoring guide-element after deploying the first anchor and before deploying the second anchor. The anchoring guide-element includes a body portion having distal and proximal ends and an anchoring portion on the distal end of the body portion. The anchoring portion is configured to be deployed from a contracted state to an expanded state that is generally transverse to the length-wise central axis of the body portion. The anchoring portion in the deployed state resists retraction of the anchoring guide-element from the heart tissue.

The steps of introducing, directing, and deploying can be performed from a primary incision site that is located substantially near a superficial vein of the lower thorax. The method can also be transferred from the primary incision site to a secondary incision site located substantially near a superficial vein of the upper thorax.

Another illustrative embodiment of the present invention includes an introducer assembly for introducing a surgical device into the vascular system. The introducer assembly includes a removable dilator and an introducer. The removable dilator has an attachment mechanism for removably attaching an introducer set. The introducer receives the removable dilator with the introducer set and maintains a puncture through the vascular wall.

In another illustrative embodiment of the present invention, a method of introducing a surgical device into the vascular network of a patient with the introducer assembly is described. The method includes attaching the introducer set to the removable dilator. The introducer set and removable dilator are received by the introducer. A guide-wire punctures a vessel wall and the introducer assembly is advanced over the guide-wire, as a unit, until the hub of the introducer contacts an external surface of the vessel. The removable dilator and introducer set are removed and a surgical device is directed through the introducer and into the vascular network.

In yet another illustrative embodiment of the present invention, a method of in vivo coupling of the flexible cannula body to the transseptal tip is described. The flexible cannula body includes a first marker on the receiving portion and the transseptal tip includes a second marker on the engaging portion. The method includes directing the flexible cannula body to the transseptal tip. The receiving portion of the cannula is coupled to the engaging portion of the transseptal tip until the first marker overlays the second marker.

Another illustrative embodiment of the present invention includes a method of aligning the flexible cannula body to the transseptal tip, in vivo. The method includes directing a cannula guide to the transseptal tip. The expandable member of the cannula guide is inflated to engage the inner surface of the transseptal tip. The cannula is advanced over the proximal taper of the cannula guide to the proximal end of the transseptal tip.

In yet another illustrative embodiment of the present invention, a method of removing a circulatory assist device is described. The method includes disengaging the flexible cannula body from the pump. The flexible cannula body is then uncoupled and retracted from the transseptal tip. The transseptal tip is then sealed.

BRIEF DESCRIPTION OF THE FIGURES

FIG. 2A is a disassembled side elevational view of a transseptal access system, including a delivery sheath, a dilator, and a transseptal needle.

FIG. 2B is an assembled side elevational view of the transseptal access system, including the delivery sheath, a dilator, and the transseptal needle.

FIGS. 3A-3C are diagrammatic views of an exemplary method of accessing the left atrium by puncturing the intra-atrial septum of the human heart, shown in partial cross-section.

FIG. 4A is a disassembled side elevational view of an anchoring guide-element and a delivery device for the anchoring guide-element, shown in partial cross-section.

FIG. 4B is an assembled side elevational view, in partial cross-section, of the anchoring guide-element and the delivery device for the anchoring guide-element.

FIG. 4C is a diagrammatic view of an exemplary method of advancing the assembled anchoring guide-element and delivery device to the left atrium of the human heart, shown in cross-section.

FIG. 5A is a disassembled side elevational view of a transseptal tip and a delivery catheter.

FIG. 5B is an assembled cross-sectional view of the transseptal tip and the delivery catheter.

FIG. 5C is a perspective view of the transseptal tip.

FIG. 6M is a side elevational view of a flexible cannula body.

FIGS. 6N-6O are diagrammatic views of an exemplary method of advancing and attaching the flexible cannula body to the transseptal tip, shown in cross-section.

FIG. 7F is a diagrammatic view of an exemplary method of sealing the transseptal tip after the flexible cannula body has been removed, shown in cross-section.

DETAILED DESCRIPTION

Figure 1:
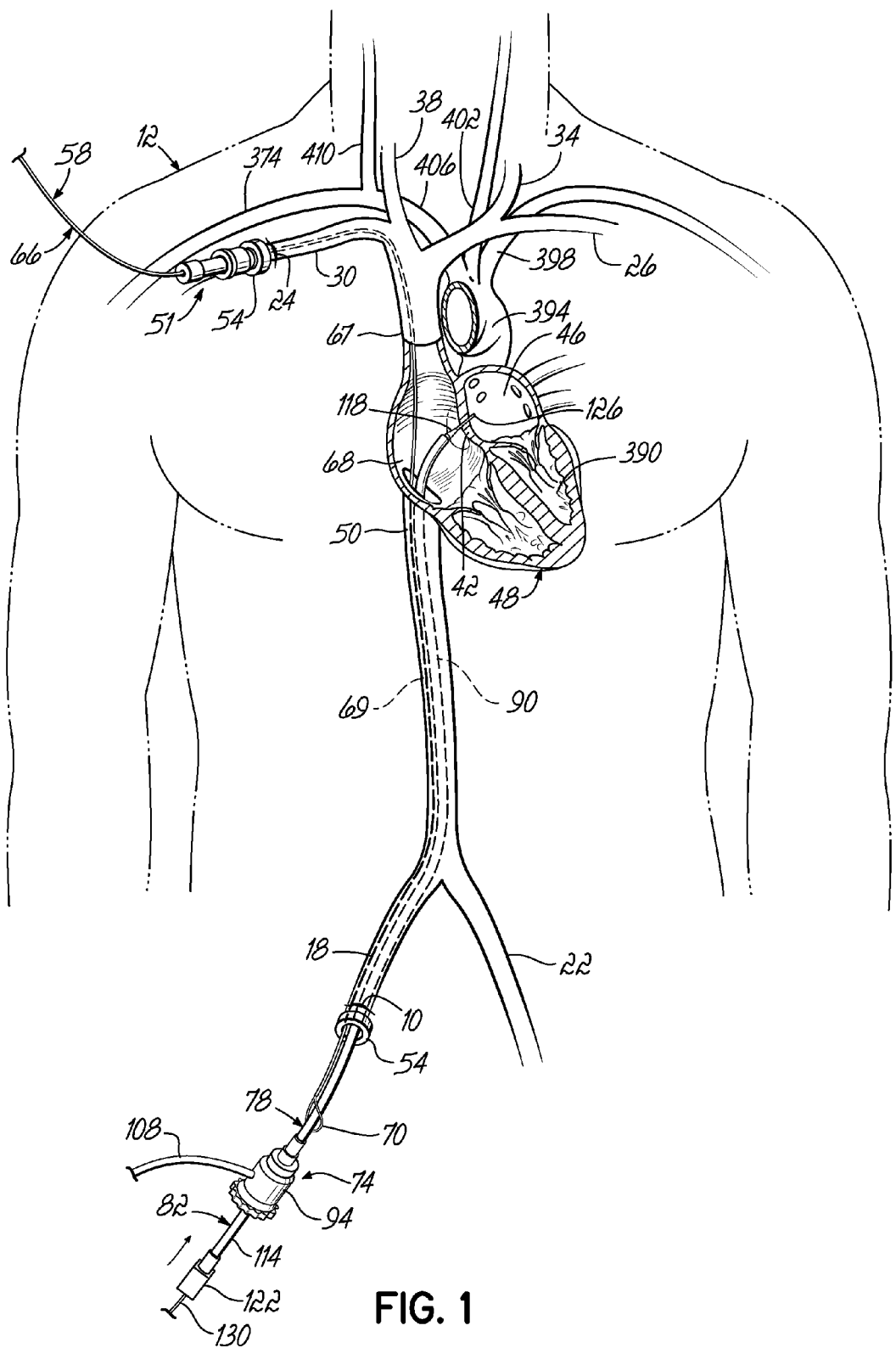
FIG. 1 is a diagrammatic view of an exemplary method of accessing the intra-atrial septum of the human heart, shown in cross-section.

Implanting a circulatory assist system can begin with a percutaneous transseptal crossing procedure. FIG. 1 illustrates a portion of the procedure where the physician creates a primary incision site 10 in a patient 12 that is substantially near a superficial vein. A suitable superficial vein for the primary incision site 10 can include a peripheral vein, such as the right or left femoral veins 18, 22, or others known by one skilled in the art. It is generally preferred that the primary incision site 10 is inferior to a secondary incision site 24 that is substantially near a peripheral vein of the upper thorax, such as the left or right subclavian veins 26, 30; the left or right jugular veins 34, 38; at the junction between the left or right subclavian vein 26, 30 and the adjoining jugular vein 34, 38; or other suitable peripheral veins known by one skilled in the art.

The use of a primary incision site 10 is preferred for accessing a heart tissue, such as an intra-atrial septum 42, due to the angle of the heart 48 with respect to the inferior vena cava 50. The primary incision site 10 is also well suited for the embodiments of the present invention because the angle between the inferior vena cava 50 and the intra-atrial septum 42 allows the physician to apply greater force for inserting a transseptal tip (described below) into the intra-atrial septum 42.

The physician may use a custom introducer assembly to create and maintain the incision into each of the superficial veins. The details of the introducer assembly 51 are shown in FIG. 1A and generally include an introducer 52 and a removable dilator 53 that are used in cooperation with commercially available introducer sets, in a manner that is described below.

The customized introducer 52 includes a hub 54 and a sheath 55 that extends distally from the hub 54. The sheath 55 of the introducer 52 is constructed from a mid-to-high durometer material such that the sheath 55, once inserted, does not collapse under the pressure of the wall of the superficial vein. The sheath material can be a high density polyethylene having a low coefficient of friction to ensure that surgical devices move with ease through the lumen of the introducer 52. Alternatively, a low friction coating can be applied thereto. In yet other embodiments, the sheath 55 can include braid or coil structures, formed from materials such as stainless steel wire, Nitinol, or other materials known in the art, to provide additional structural stability when needed. Generally, the sheath 55 of the introducer 52 should be sufficient in length to extend within the lumen of the superficial vein while the hub 54 remains proximal to the incision site. A suitable length can be about 10 cm; however, this should not be considered limiting.

The hub 54 of the introducer 52 includes a sealing mechanism, illustrated herein as an O-ring 56, for sealing against the removable dilator 53 or any other subsequently introduced surgical device. Accordingly, the O-ring 56 should have an inner diameter that is sufficiently equal to the nominal outer diameter of the removable dilator 53. Because the O-ring 56 would not prevent bleeding through the introducer 52 once the removable dilator 53 has been removed, a silicone plug (not shown) can be used to seal the hub 54 of the introducer 52 at the O-ring 56. Alternatively, other sealing mechanisms, such as a hemostatic seal or a grommet, can be used. The hemostatic seal or grommet would automatically provide a fluidic seal against the interstitial pressures when the removable dilator 53 or other surgical device is not present in the introducer 52.

Figure 1A:
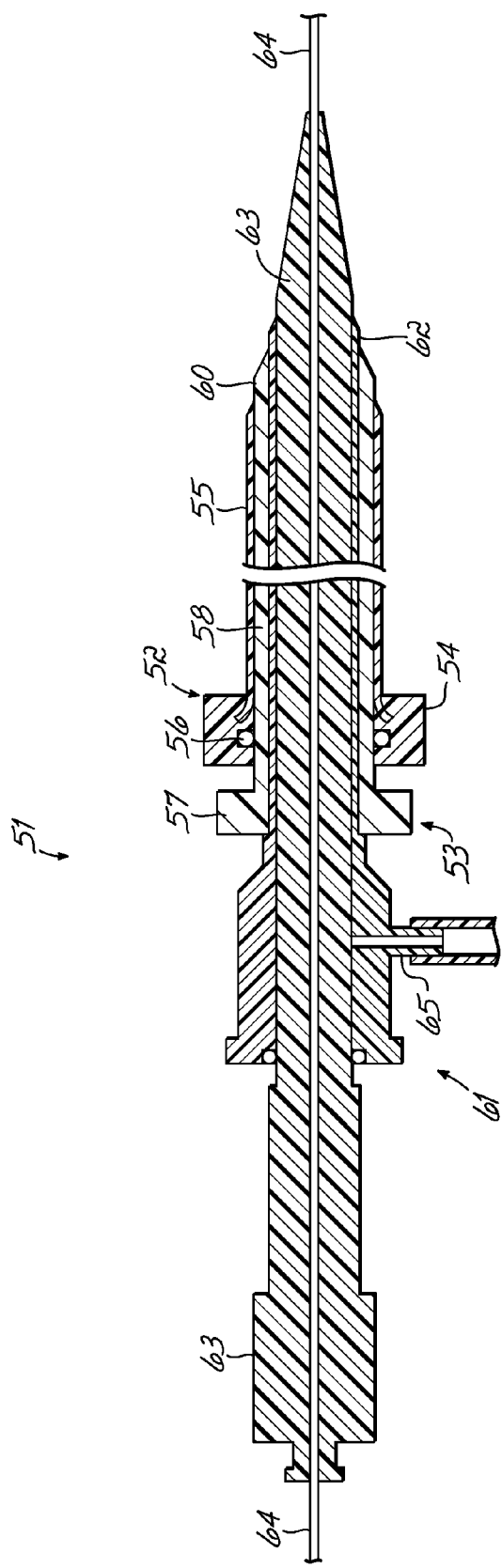
FIG. 1A is an assembled side elevational view of an introducer assembly, shown in cross-section.

FIG. 1A further illustrates the details of the removable dilator 53, which include a hub 57 and a dilator sheath 58 extending distally from the hub 57. The dilator sheath 58 can be formed by a melt flow process to create a distal taper 60 as an attachment mechanism for attaching to an introducer set 61. For example, the distal taper 60 forms a frictional fit with the introducer set 61, which is conventionally used for obtaining vascular access. Suitable introducer sets 61 may include those that are commercially available, such as the COOK CHECK-FLO PERFORMER introducer set having a sheath introducer 62, a dilator 63, and a guide-wire 64. The distal taper 60 can be constructed to fit any commercially available introducer set 61 having a particular size, for example those having 12.0 French or 6.0 French dilators. In some embodiments, the sheath introducer 62 can include a flushing side-arm port 65 for removing fluid from the incision site.

Though not specifically shown, the hub 57 of the removable dilator 53 can include a proximal seal as the attachment mechanism in alternative or in addition to the distal taper 60. Suitable proximal seals can include, for example, an O-ring to proximally couple and seal the removable dilator 53 against the introducer set 61.

In operation, the commercial introducer set 61 is inserted through the lumen of the removable dilator 53, which is then, in turn, loaded into the introducer 52. The guide-wire 64 of the introducer set 61 is advanced to puncture the wall of the superficial vein. The introducer set 61, removable dilator 53, and introducer 52 are then backloaded, as a unit, over the guide-wire 64 and to the wall of the superficial vein. The puncture within the wall of the superficial vein undergoes a first dilation to a first diameter with the dilator 63 and then a second dilation to a second diameter by the removable dilator 53. Finally, with continued advancement, the sheath 55 of the introducer 52 enters the lumen of the superficial vein until a distal end of the hub 54 of the introducer 52 contacts an external surface of the incision site. If desired, the guide-wire 64 can then be removed from the superficial vein.

The introducer 52, removable dilator 53, and introducer set 61 can remain within the wall of the superficial vein, as a unit, until a larger surgical device is needed. Accordingly, the physician can decouple the removable dilator 53 with the introducer set 61, as a unit, from the introducer 52. The introducer 52 remains extended through the wall of the superficial vein to maintain a vascular network access point, which allows the physician to advance larger surgical devices into the vascular network with little to no friction from the contracting wall of the superficial vein.

Referring again to FIG. 1, once the primary and secondary incision sites 10, 24 are made, and the custom introducer assembly is properly positioned, the physician can direct a capture device, such as a standard snare device 66, from the secondary incision site 24, down the superior vena cava 67, the right atrium 68, the inferior vena cava 50, the right femoral vein 18, and out of the primary incision site 10. The standard snare device 66 can include a body 69 that extends between the primary and secondary incision sites 10, 24 and a snare loop 70 on a distal end of the body 69. Though not shown, in some embodiments, the snare loop 70 can remain within the right femoral vein 18 and not extend externally from the primary incision site 10.

The method continues with the physician removing the dilator 53 (FIG. 1A) and the introducer set 61 (FIG. 1A) from the hub 54 of the introducer 52 extending from the primary incision site 10 to allow passage of a transseptal access system 74 into the vascular network for making a percutaneous transseptal crossing. The transseptal access system 74 is then inserted through the snare loop 70, into the primary incision site 10, up the right femoral vein 18, the inferior vena cava 50, and into the right atrium 68. It would be understood that the introducer assembly 51 remains fully assembled at the secondary incision site 24.

FIG. 2A illustrates the details of the disassembled transseptal access system 74, which includes a delivery sheath 78, a dilator 82, and a transseptal needle 84.

The delivery sheath 78 has a flexible body 90 with a distal end, a proximal end, and a lumen extending between. A hub 94 is positioned on the proximal end of the flexible body 90. The flexible body 90 of the delivery sheath 78 is custom sized to facilitate the delivery of a transseptal tip (discussed below) and can be constructed as three thin-layer walls. The exterior layer can be constructed of materials such as polyurethane, Nylon-11, Nylon-12, or PEBAX, thermoplastic elastomers, copolymers, or blends of urethanes; the interior layer can be a liner made from etched polytetrafluorethylene (ePTFE), urethane, or Nylon with hydrogel coating; and the mid-layer can be constructed from a braided material or a coiled member, such as stainless steel wire, Nitinol, or polyetheretherketones (PEEK) fibers to provide structural stability to the flexible body 90. The interior layer, or liner, can be extruded and placed upon a mandrel with the midlayer and the exterior layer respectively formed or otherwise placed over the interior layer. Polyurethane is then placed over the entire assembly and heat shrink wrapped over the flexible body 90 for stability. Alternatively, the flexible body 90 of the delivery sheath 78 can be laminated by a reflow process. In some instances, a superelastic coil (nickel titanium, NiTi, or stainless steel) or a metallic braid can be included to further increase the rigidity of the delivery sheath 78. The superelastic coil or metallic braid can enhance the maneuverability of the flexible body 90. A polymeric layer can surround the superelastic coil or braid to reduce friction as the flexible body 90 moves within the vascular network. It would also be permissible for the flexible body 90 to include a lubricious material, such as HYDROMED or a polyamide, to reduce friction as a delivery catheter (described below) moves within the flexible body 90.

In some embodiments, the flexible body 90 can further include a marker 98 constructed from a metallic material, such as gold (Au) or platinum (Pt), or from a polymeric material embedded with a dense powder, such as tungsten (W). The marker 98 aids the physician in positioning the delivery sheath 78 in vivo.

The hub 94 of the delivery sheath 78 can include a main port 102 having a hemostasis valve (described below) to prevent blood from exiting the delivery sheath 78 during the introduction and/or removal of other surgical devices, such as the dilator 82. A side port 106 permits limited fluidic access via a tubing 108 and a valve 110.

Referring still to FIG. 2A, the details of the dilator 82 will now be described. The dilator 82 has a dilator body 114, a dilator tip 118, and a dilator hub 122. The dilator body 114 is custom sized to facilitate the delivery of the transseptal tip (discussed below). The dilator body 114 and dilator tip 118 can be constructed from a polymer with a low coefficient of friction, such as fluoropolymer. The dilator tip 118 should be constructed with sufficient rigidity to dilate an opening through the heart tissue. The dilator hub 122 allows the dilator 82 to be flushed with saline prior to insertion into the vascular network.

In some embodiments, it would be permissible for the distal ends of the delivery sheath 78 and the dilator 82 to include a preformed shape that is directed toward the intra-atrial septum 42 (FIG. 1).

FIG. 2A also illustrates the transseptal needle 84, which can be any device that has a hollow needle tip 126, a hollow needle body 130, and a needle hub 134, such as the Brockenbrough transseptal needle. The needle hub 134 can be used in monitoring the patient's blood pressure while the transseptal needle 84 punctures the intra-atrial septum 42 (FIG. 1).

FIG. 2B illustrates the assembled transseptal access system 74.

Figure 3C:
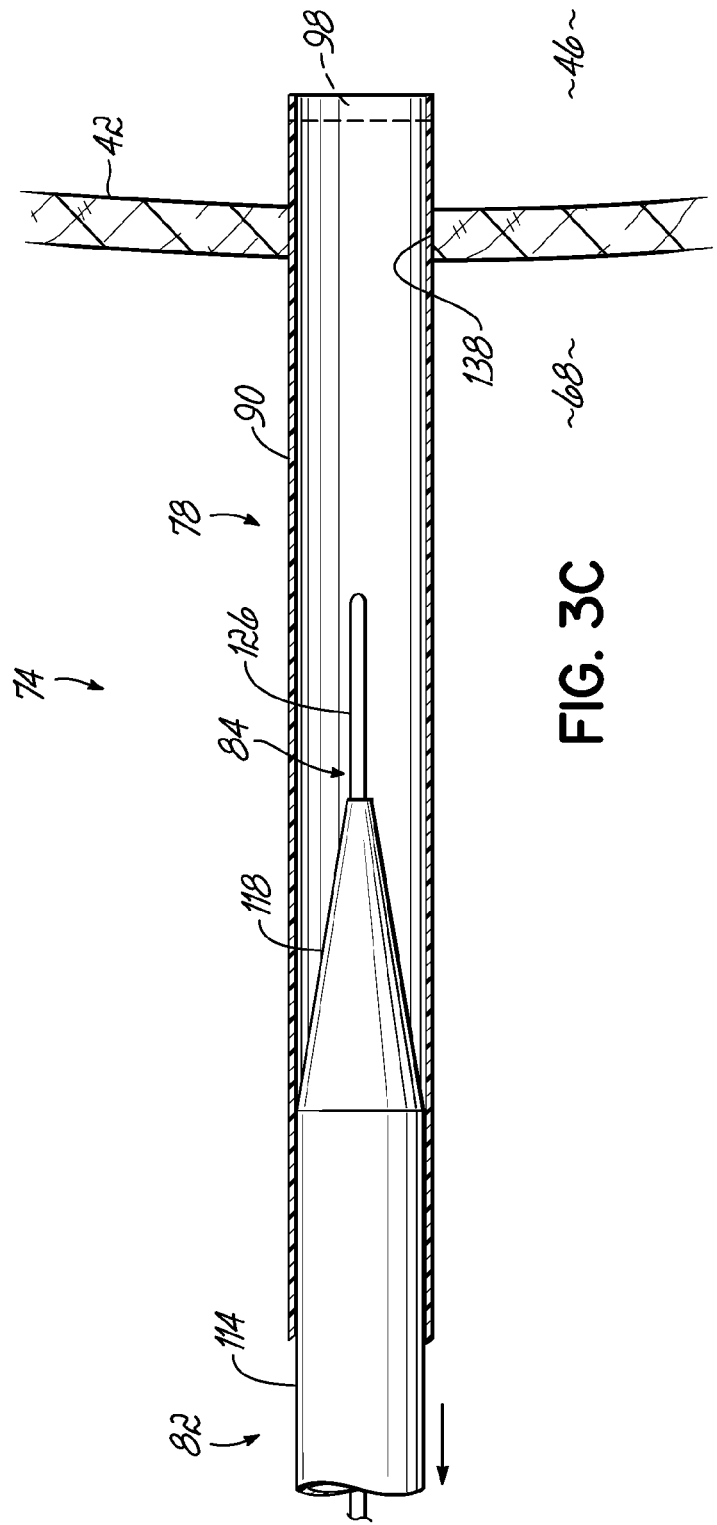

With the details of the transseptal access system 74 described in some detail, the method of percutaneous transseptal crossing can continue with reference to FIGS. 3A-3C.

FIG. 3A illustrates the transseptal access system 74 as the transseptal needle 84 creates a puncture 138 in the intra-atrial septum 42 and enters the left atrium 46. The dilator tip 118 is then advanced over the transseptal needle 84 and dilates the puncture 138 through the intra-atrial septum 42.

FIG. 3B illustrates the continued advancement of the dilator 82 such that the puncture 138 is further dilated to a diameter that is approximately equal to the diameter of the dilator body 114. This further dilation allows the delivery sheath 78 to advance over the dilator 82, through the dilated puncture 138, and to enter the left atrium 46. Once the delivery sheath 78 is within the left atrium 46, the dilator 82 and the transseptal needle 84 are retracted, as illustrated in FIG. 3C.

With the delivery sheath 78 (FIG. 3C) in place, the physician can then use an anchoring guide-element to aid in the method of implanting the transseptal tip (discussed below). The anchoring guide-element may then also be used to facilitate the redirecting of the implanting procedure from the primary incision site 10 (FIG. 1) to the secondary incision site 24 (FIG. 1).

FIG. 4A illustrates an exemplary embodiment of the anchoring guide-element 142, though additional detail is provided in U.S. patent application Ser. No. 12/256,911. The anchoring guide-element 142 has a body portion 146 and an anchoring portion 150 on the distal end of the body portion 146.

The body portion 146 can be constructed from a central core made from a metallic material, such as stainless steel or nickel titanium (NiTi) and covered with a polymeric material to reduce the friction between the anchoring guide-element 142 and any surgical device that is advanced over the anchoring guide-element 142. The body portion 146 should be flexible enough to prolapse upon itself. The proximal end of the body portion 146 may include an atraumatic coil 154 constructed from wound radiopaque metal wire (for example, platinum (Pt)).

The anchoring portion 150 has a plurality of struts 158 attached to a hub 160. The hub 160 has a tip transition section 162, a strut retaining ring 166, and a tip 170. The tip 170 can be machined from a dense, radiopaque metallic material, such as platinum (Pt) or tantalum (Ta), and coated with a material to prevent galvanic corrosion with the plurality of struts 158. The tip 170 secures the body portion 146 to the anchoring portion 150 by either laser welding or a chemical bonding process. The strut retaining ring 166 can be constructed of similar material as the tip 170 and secures the plurality of struts 158 to the anchoring portion 150. The tip transition section 162 can be constructed of similar materials but should be devoid of any sharp edges that may catch or snag on other surgical devices when removing the anchoring guide-element 142.

The plurality of struts 158 can be constructed from a sheet of superelastic, metallic material (e.g. NiTi) or MP35N, which allows each of the plurality of struts 158 to be folded and/or held in a position that is parallel to central axis of the body portion 146. Once released, the plurality of struts 158 will automatically spring to a deployed state that is transverse to the central axis. While four struts 158 are shown, this number is not so limited. Rather, embodiments could be envisioned where two struts or up to eight struts can be necessitated for a particular physician's needs or preference.

Continuing with FIG. 4A, a delivery device 174 for the anchoring guide-element 142 is shown. A sheath tip 178 of the delivery device 174 receives the proximal end of the body portion 146 of the anchoring guide-element 142. As the body portion 146 is pulled through the sheath tip 178 and a sheath body 182, the plurality of struts 158 contacts the sheath tip 178 and is folded from the position transverse to the central axis to the position that is parallel to the central axis. The sheath body 182 is constructed from etched polytetrafluorethylene (ePTFE) or fluorinated ethylene propylene (FEP) so as to allow minimal clearance between the lumen of the sheath body 182 and the body portion 146 of the anchoring guide-element 142. This construction facilitates the delivery of the anchoring guide-element 142 because the body portion 146 construction of the anchoring guide-element 142 lacks sufficient column strength to advance the folded plurality of struts 158 through the delivery sheath 78 (FIG. 3C) to the desired location. This minimal clearance can further aid the physician in deploying the plurality of struts 158.

FIG. 4B illustrates the anchoring guide-element 142 fully loaded within the delivery device 174 with the plurality of struts 158 deflected to the position parallel to the central axis. The delivery device 174 and anchoring guide-element 142 are then ready to be back-loaded through the hub 94 (FIG. 2A) of the delivery sheath 78 (FIG. 2A).

FIG. 4C illustrates the advancement of the delivery device 174 and the anchoring guide-element 142 through the delivery sheath 78 until the distal end of the sheath tip 178 begins to emerge from the delivery sheath 78.

Figure 5D:
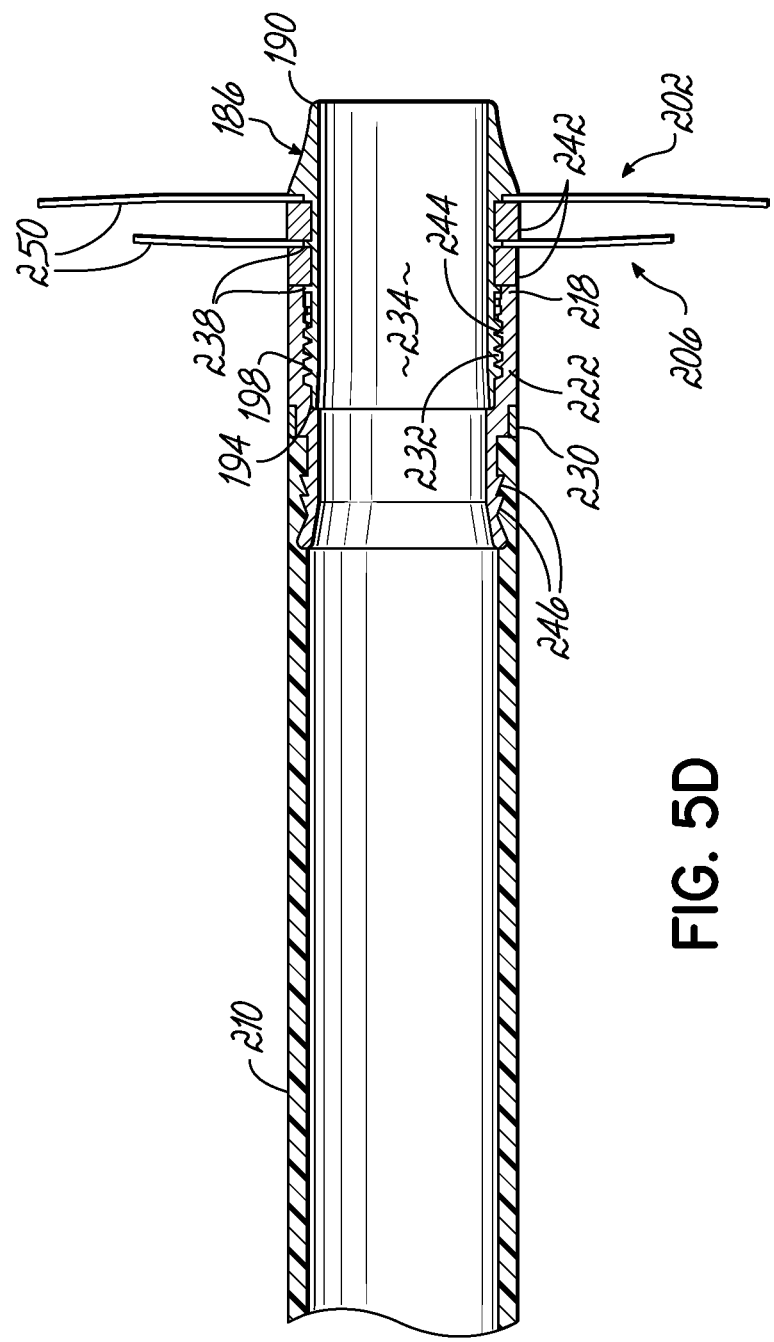
FIG. 5D is an assembled cross-sectional view of the transseptal tip and the delivery catheter.

The method for implanting the transseptal tip 186 now continues with reference to FIGS. 5A-5E. FIG. 5A illustrates the details of the transseptal tip 186, which include a distal end 190 and a proximal end 194 having an engaging portion 198. The engaging portion 198 is operable to connect to a receiving portion (described below) of a flexible cannula body (described below) or a receiving portion of a delivery catheter (described below) in vivo. In a preferred embodiment, the transseptal tip 186 is constructed from titanium alloy, such as TiAl 6Va EL 1, by standard turning, wire electrical discharge machining (EDM), or other machining processes. Alternatively, the transseptal tip 186 can be constructed from a polymeric material (for example, nylon) that is compounded using radiopaque filler that is typically encapsulated within the polymer matrix. The radiopaque filler can include platinum-iridium (Pt:Ir), stainless steel, tungsten (W), or tantalum (Ta) and allows for the in vivo visualization of the transseptal tip 186 by non-invasive devices, such as X-ray, real-time fluoroscopy, or intracardiac echocardiograph.

First and second anchors 202, 206 are coupled to the transseptal tip 186. The first and second anchors 202, 206 are configured to be deployed from a contracted state to an expanded state. Once in the expanded state, the first anchor 202 will engage the intra-atrial septum 42 (FIG. 1) within the left atrium 46 (FIG. 1) while the second anchor 206 will engage the intra-atrial septum 42 (FIG. 1) within the right atrium 68 (FIG. 1). Additionally, it is possible to construct the first and second anchors 202, 206 in a way such that the second anchor 206 is larger than the first anchor 202. This configuration is more desirable than the reverse because the right atrium 68 (FIG. 1) is larger in volume than the left atrium 46 (FIG. 1); however, the invention should not be considered so limited. While the first and second anchors 202, 206 are described in some detail below, additional details and features are disclosed in U.S. patent application Ser. No. 12/256,911.

Continuing with FIG. 5A, the delivery catheter 210 for the transseptal tip 186 is shown. The delivery catheter 210 has a proximal end 214 and a distal end 218 that includes a receiving portion 222. The receiving portion 222 is operable to removably disengage the engaging portion 198 of the transseptal tip 186 in vivo. The delivery catheter 210 can be made from a polymer (such as Pebax or polyurethane) and can be reinforced with a metallic coil 226 or braid (not shown) or stiffening stylet to enhance the response of the delivery catheter 210. To further increase the torque response, the coil 226 can be constructed to wind in a direction that is similar to the direction of rotation used to disengage the receiving portion 222 from the engaging portion 198. The delivery catheter 210 can further include a marker 230 near the distal end 218 of the delivery catheter 210. The marker 230 may be constructed from a radiopaque material to enhance in vivo visualization.

FIG. 5B illustrates the transseptal tip 186 and the delivery catheter 210 with greater detail. The engaging portion 198 can be constructed as a low profile, coarse, male thread 232 for threadably engaging the receiving portion 222 of the delivery catheter 210 or of the flexible cannula body (described below). The low profile and coarse construction of the thread 232 aids in preventing cross threading during the in vivo disassembly of the transseptal tip 186 from the delivery catheter 210 or during the in vivo assembly of the flexible cannula body, described in detail below. The threads 232 can be molded as part of the transseptal tip 186 during construction. Alternatively, the threads 232 are machined after molding and polished to remove any rough edges.

In another embodiment, not specifically shown, the engaging portion 198 can include a first magnet with a polarity that is opposite to a second magnet on the receiving portion 222 of the delivery catheter 210. The magnetic field between the first and second magnets should be sufficiently strong to resist decoupling without an appropriate amount of force. Generally, the magnetic field should be sufficiently strong to resist decoupling of the receiving portion 222 from the engaging portion 198 due to the frictional force of blood pumping through the transseptal tip 186 and flexible cannula body (described below). Other alternative means of engaging can include adhesives or frictional fit.

The distal end 190 of the transseptal tip 186 is shown to include a shape that will reduce fluidic drag and can be coated with a material that prevents thrombus growth; however, the transseptal tip 186 should not be considered to be limited to the shape specifically shown.

The transseptal tip 186 also includes a lumen 234 extending between the distal and proximal ends 190, 194. Once the transseptal tip 186 is implanted, the lumen 234 creates a shunt through the intra-atrial septum 42 (FIG. 1).

The transseptal tip 186 can further include one or more rings 238 provided for several reasons. These rings 238 can act in a manner such as to engage the first and second anchors 202, 206. In this way, the rings 238 can act in conjunction with clamps 242 to affix the first and second anchors 202, 206 on the transseptal tip 186. The rings 238 could also be used in seating the first and second anchors 202, 206 and keyed in a way so as to maintain an orientation of the first and second anchors 202, 206. Suitable clamps 242 can include configurations as shown or others such as, but not limited to, swage or crimp-style clamps. The clamps 242 could alternately be attached to the transseptal tip 186 by adhesive, welding, or tying.

In construction, the rings 238 can advantageously be molded as a portion of the transseptal tip 186. Alternatively, the rings 238 are swaged or crimped into place after the transseptal tip 186 is constructed. In some embodiments, the rings 238 can optionally be constructed of radiopaque materials such as to aid in localization of the transseptal tip 186. Alternatively, a separate radiopaque band (not shown) can be constructed and placed sufficiently near the rings 238.

FIG. 5B further illustrates that the receiving portion 222 of the delivery catheter 210 may be constructed as the female counterpart thread 244 to the thread 232 of the engaging portion 198. The threads 244 of the delivery catheter 210 can be constructed from a radiopaque material to allow for fluoroscopic visualization, from a polished metallic material (such as titanium (Ti)), or from a molded polymeric material (such as nylon) that is compounded using radiopaque filler (such as tantalum (Ta)). The proximal end of the receiving portion 222 can further include one or more barbs 246. Barbs 246 provide resistance against the undesired removal of the receiving portion 222 from the delivery catheter 210. A tie (not shown) can also be included external to the delivery catheter 210 at the barbs 246 to further secure the delivery catheter 210 to the receiving portion 222. In some embodiments, the proximal end can include a shape that will reduce fluidic drag; however, the proximal end should not be considered to be limited to the shape specifically shown.

FIG. 5C illustrates with greater detail the transseptal tip 186 with the first and second anchors 202, 206. Each of the first and second anchors 202, 206 generally includes a plurality of struts 250 extending from a central ring portion (not shown) such that the plurality of struts 250 and central ring portion are etched as a single unit from the same piece of superelastic material. Alternatively, it would be possible to permanently affix each of the plurality of struts 250 to a separately manufactured central ring portion, such as by welding or other means. It should be appreciated that while four struts are shown per anchor 202, 206, this number is not so limited. Rather, embodiments could be envisioned where fewer or more struts can be necessitated for a particular physician's needs or preference. Generally, three or more struts are preferred.

The first and second anchors 202, 206 can be at least partially constructed from a superelastic material (such as nickel titanium (NiTi)) or by chemically etching the parts from flat sheet stock, electropolishing the etched parts to remove rough edges generated during the formation process, and then heating the parts to a superelastic state. While the preferred materials are specifically taught herein, other suitable biocompatible, non-compliant, flexible material would be sufficient for the transseptal tip 186 or the anchors 202, 206.

FIG. 5C also illustrates that the first anchor 202 can be offset with respect to the second anchor 206. This is the preferred configuration of the deployed anchors 202, 206 because of the particular load-bearing benefits. However, it would also be possible to include anchors 202, 206 with no offset if the particular need would arise, though this is not shown.

As illustrated in phantom in FIG. 5C, the anchors 202, 206 can each respectively include a porous polymeric structure 252 over the plurality of struts 250. In function, the porous polymeric structure 252 provides a larger surface to engage the intra-atrial septum 42 (FIG. 1) than the plurality of struts 250 alone. Further, the porous polymeric structure 252 allows for tissue in-growth, where the tissue can grow and become embedded within the porous polymeric structure 252 to provide greater structural stability and sealing capacity. While either or both of the anchors 202, 206 can include the porous polymeric structure 252, it is generally preferred that only the second anchor 206, which will reside along the intra-atrial septum 42 (FIG. 1) within the right atrium 68 (FIG. 1), will include the porous polymeric structure 252. This configuration is preferred because the right atrium 68 (FIG. 1) is larger in volume than the left atrium 46 (FIG. 1); however, the invention should not be considered so limited. Suitable materials for the porous polymeric structure 252 can include, but are not limited to, polyester monofilament or multifilament yarn; ePTFE monofilament or multifilament yarn; or fluorinated polyolefin fibers or yarns, which can be woven, braided, knitted, or felted into a proper configuration. The porous polymeric structure 252 can further include various intrinsic configurations including weaves, braids, or knits having two or three-dimensional honeycombs, circular, flat, or tri-axial tubular structures. In other embodiments, the porous polymeric structure 252 can be constructed from an ePTFE piece in tubular, cylindrical, or sheet form. Generally, the porous polymeric structure 252 will be constructed by etching or laser cutting a shape from two sheets of a stock material (such as those described above). The shaped polymeric structures 252 are then ultrasonically welded together such that the shaped polymeric structures 252 capture the plurality of struts 250 therebetween.

FIG. 5D illustrates the assembled delivery catheter 210 and transseptal tip 186.

Figure 5E:
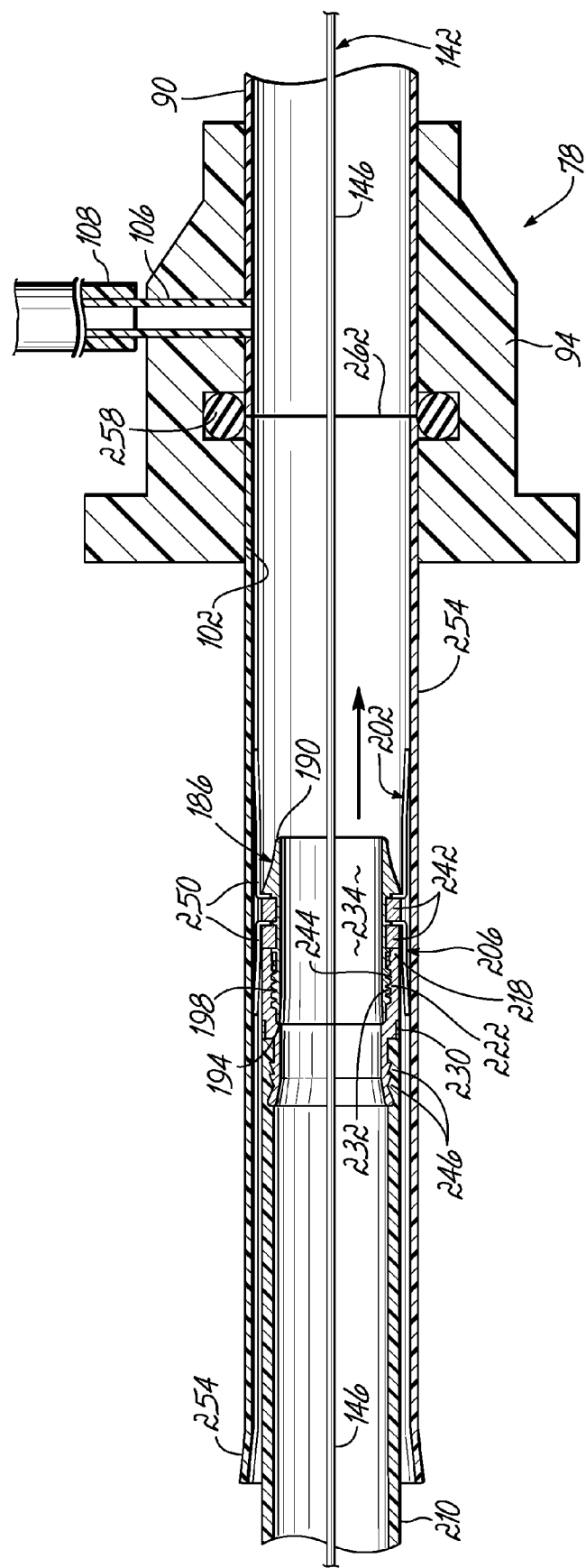
FIG. 5E is a diagrammatic view of an exemplary method of loading the assembled transseptal tip and delivery catheter into a hub of a delivery sheath.

FIG. 5E illustrates an exemplary method of loading the assembled delivery catheter 210 and transseptal tip 186 into the hub 94 of the delivery sheath 78. Because the first and second anchors 202, 206 naturally expand to a position that is transverse to the lengthwise central axis, it is necessary to fold the first and second anchors 202, 206 to a position that is parallel to the lengthwise central axis and thus suitable for loading the first and second anchors 202, 206 into the delivery sheath 78. Various manners of folding the first and second anchors 202, 206 are disclosed in U.S. patent application Ser. No. 12/256,911; however, other methods of folding the anchors 202, 206 would be known. For example, the physician can simply deflect the first anchor 202 distally while the second anchor 206 is deflected proximally. The proximal and distal folding of the anchors 202, 206 is preferred because this configuration provides the greatest distance between the folded anchors 202, 206 and can enhance the physician's control over the delivery of the anchors 202, 206. A loading tube 254 is used to open the hemostatic valve 258 within the hub 94 of the delivery sheath 78 to permit passage of various surgical devices into the lumen of the delivery sheath 78. The inner diameter of the loading tube 254 should be sufficiently similar to the inner diameter of the delivery sheath 78 to create a smooth transition 262 from the loading tube 254 and the delivery sheath 78. A positive stop (not shown) within the hub 94 provides a tactile feedback to the physician to ensure that the loading tube 254 is properly seated prior to advancing the transseptal tip 186. The loading tube 254 can be constructed from a polymer (fluoropolymer) that minimizes friction with the transseptal tip 186.

With the transseptal tip 186 and the anchors 202, 206 now loaded into the delivery sheath 78, the method of introducing the transseptal tip 186 to the intra-atrial septum 42 (FIG. 1) can proceed as shown in FIGS. 6A-6H.

Figure 6A:
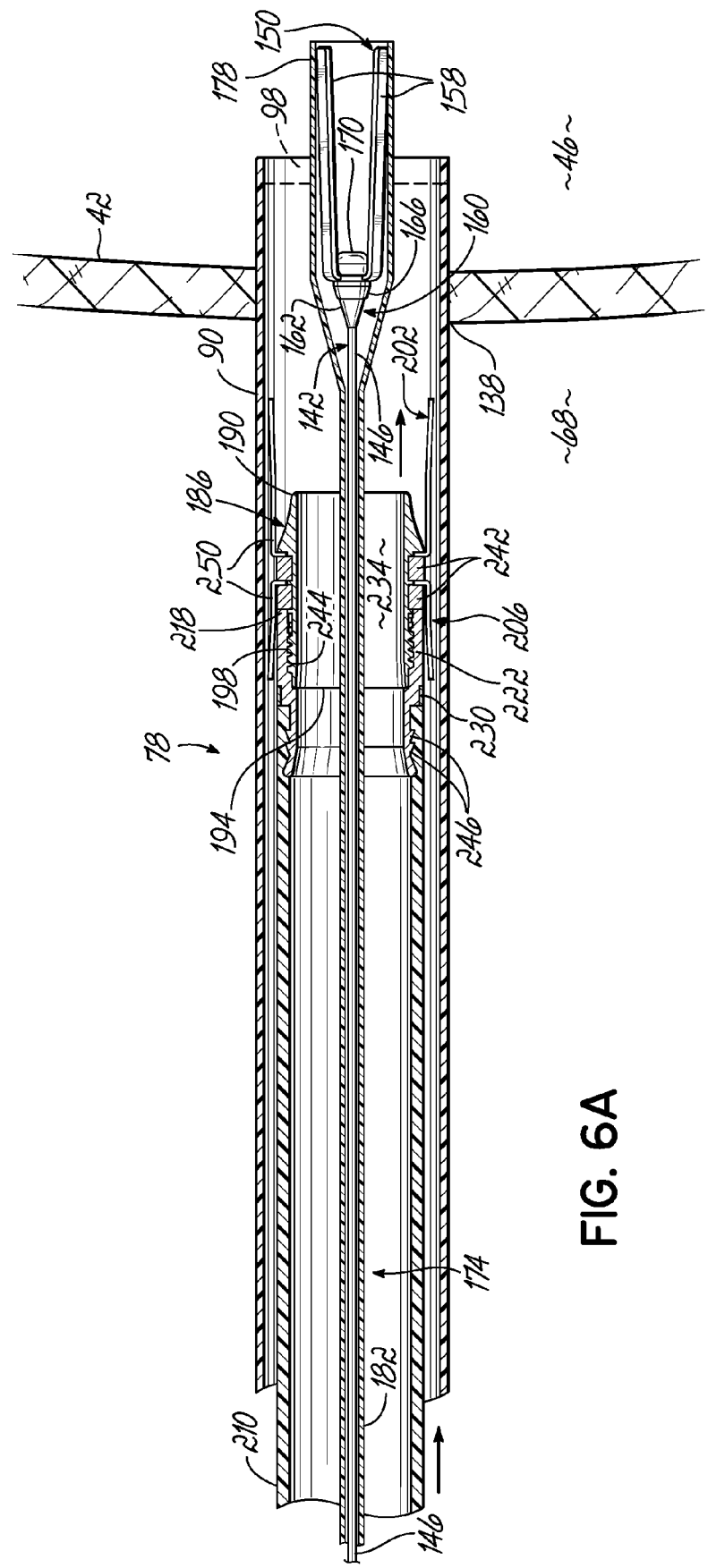
FIGS. 6A-6D are diagrammatic views of an exemplary method of deploying a first anchor of the transseptal tip and the plurality of struts of the anchoring guide-element within the left atrium, shown in cross-section.

FIG. 6A illustrates the transseptal tip 186 that has been advanced to the intra-atrial septum 42 within the right atrium 68. The transseptal tip 186 can then be advanced to the distal end of the delivery sheath 78.

Figure 6B:
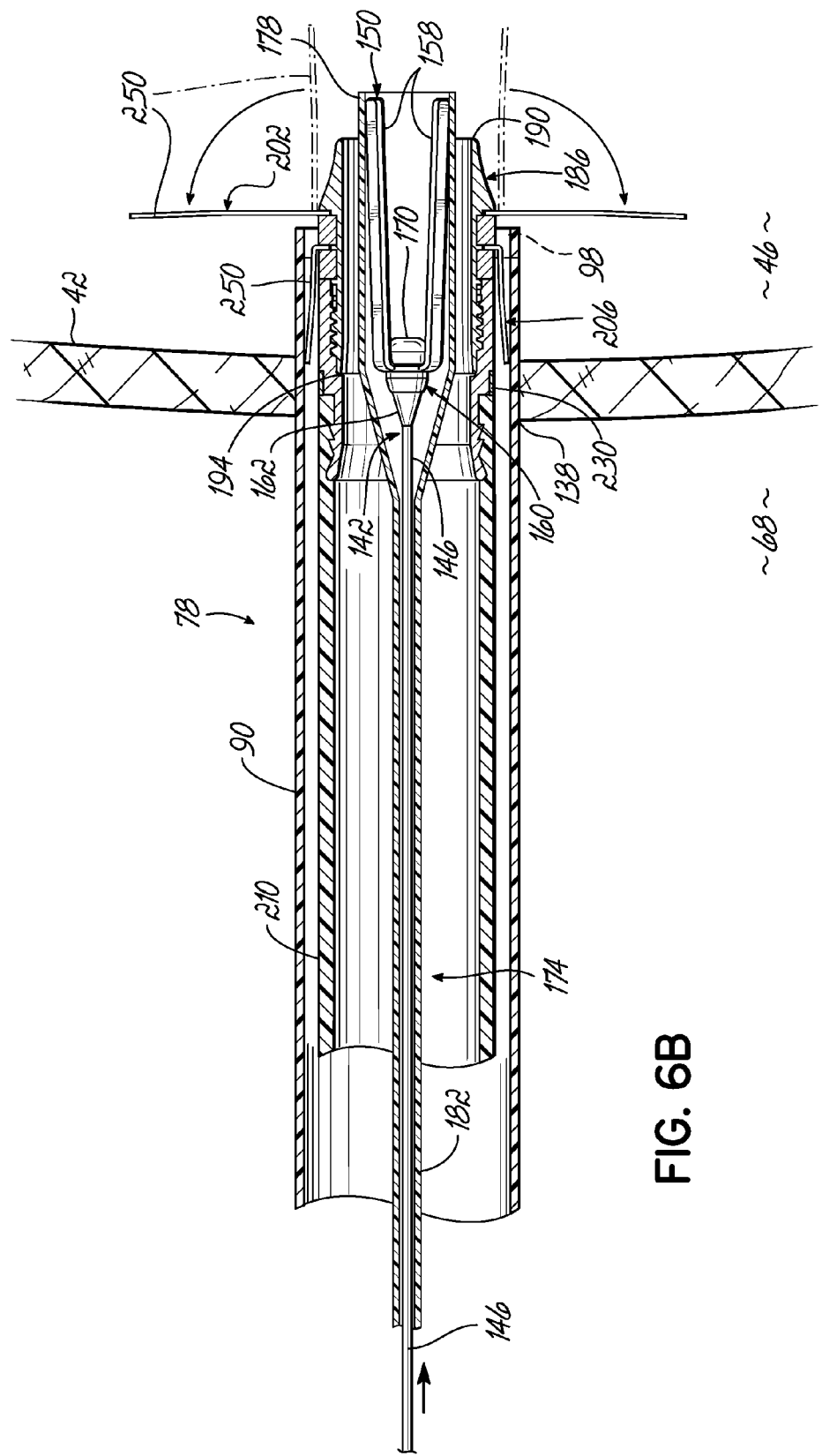

Deploying the first anchor 202, as illustrated in FIG. 6B, begins with the physician confirming that the transseptal tip 186 is advanced to the distal end of the delivery sheath 78 within the left atrium 46. The confirmation can be accomplished by in vivo localization of the marker 230 near the intra-atrial septum 42. After the confirmation, the delivery catheter 210 and transseptal tip 186 are advanced further into the left atrium 46 while the delivery sheath 78 is held in position. In this way, the transseptal tip 186 extends beyond the delivery sheath 78, and the first anchor 202 is deployed within the volume of the left atrium 46. Once deployed, the first anchor 202 can have a diameter that is at least about 1.1 times, but smaller than about 3 times, the diameter of the puncture 138 through the intra-atrial septum 42 created by the transseptal tip 186; however, the diameter of the first anchor 202 in the expanded state is limited primarily by the patient's anatomy. The physician can ensure proper deployment of the first anchor 202 by in vivo visualization of a radiopaque marker (not shown) on the plurality of struts 250 of the first anchor 202.

Figure 6C:
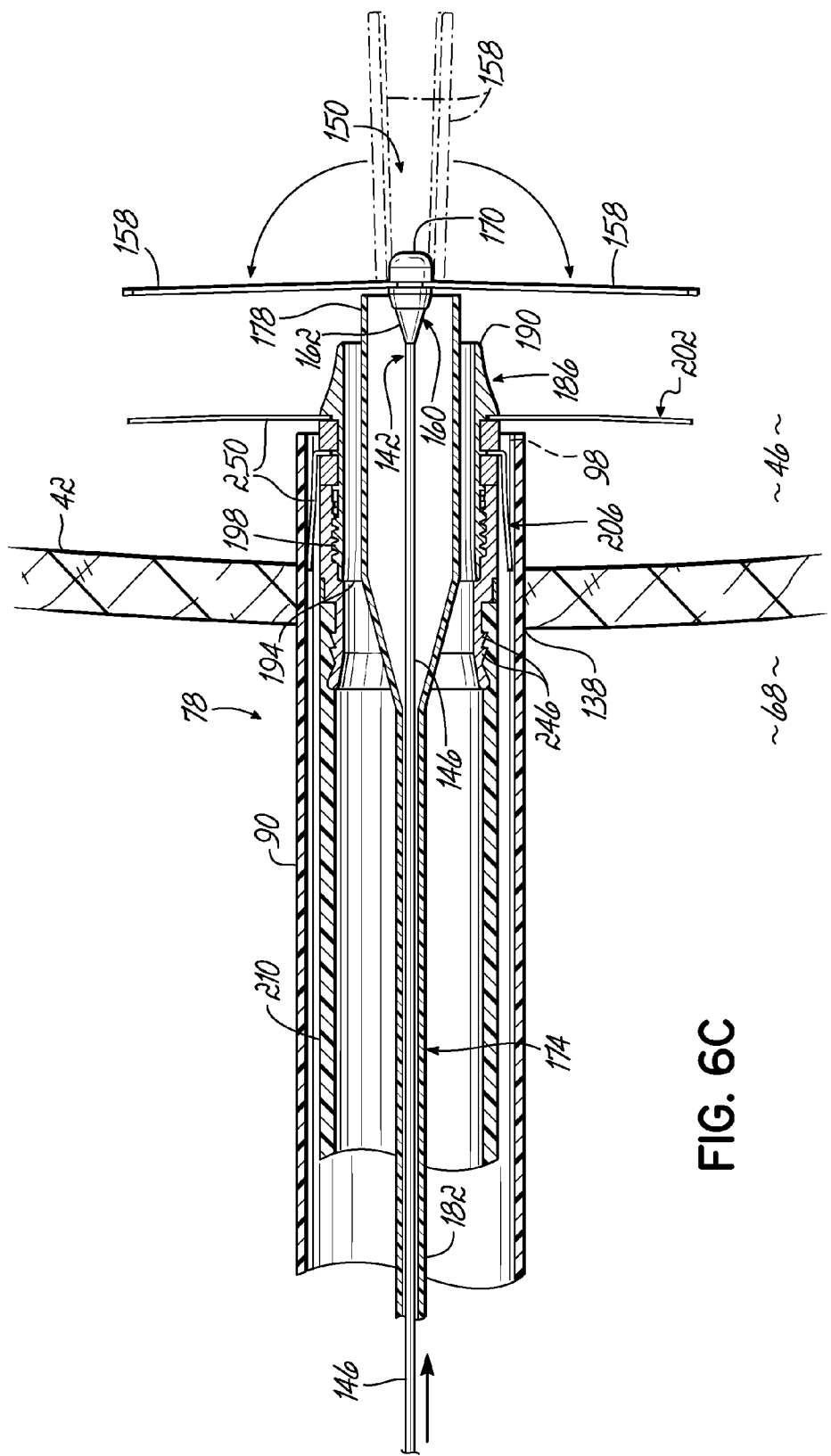

Once the proper deployment of the first anchor 202 is confirmed, the plurality of struts 158 of the anchoring guide-element 142 can be deployed, as shown in FIG. 6C. Accordingly, the position of the transseptal tip 186 is maintained while the anchoring portion 150 of the anchoring guide-element 142 is advanced beyond the sheath tip 178. In this way, the plurality of struts 158 is deployed within the volume of the left atrium 46. The physician can ensure proper deployment of the plurality of struts 158 by in vivo visualization of a radiopaque marker (not shown) on the plurality of struts 158.

Figure 6D:
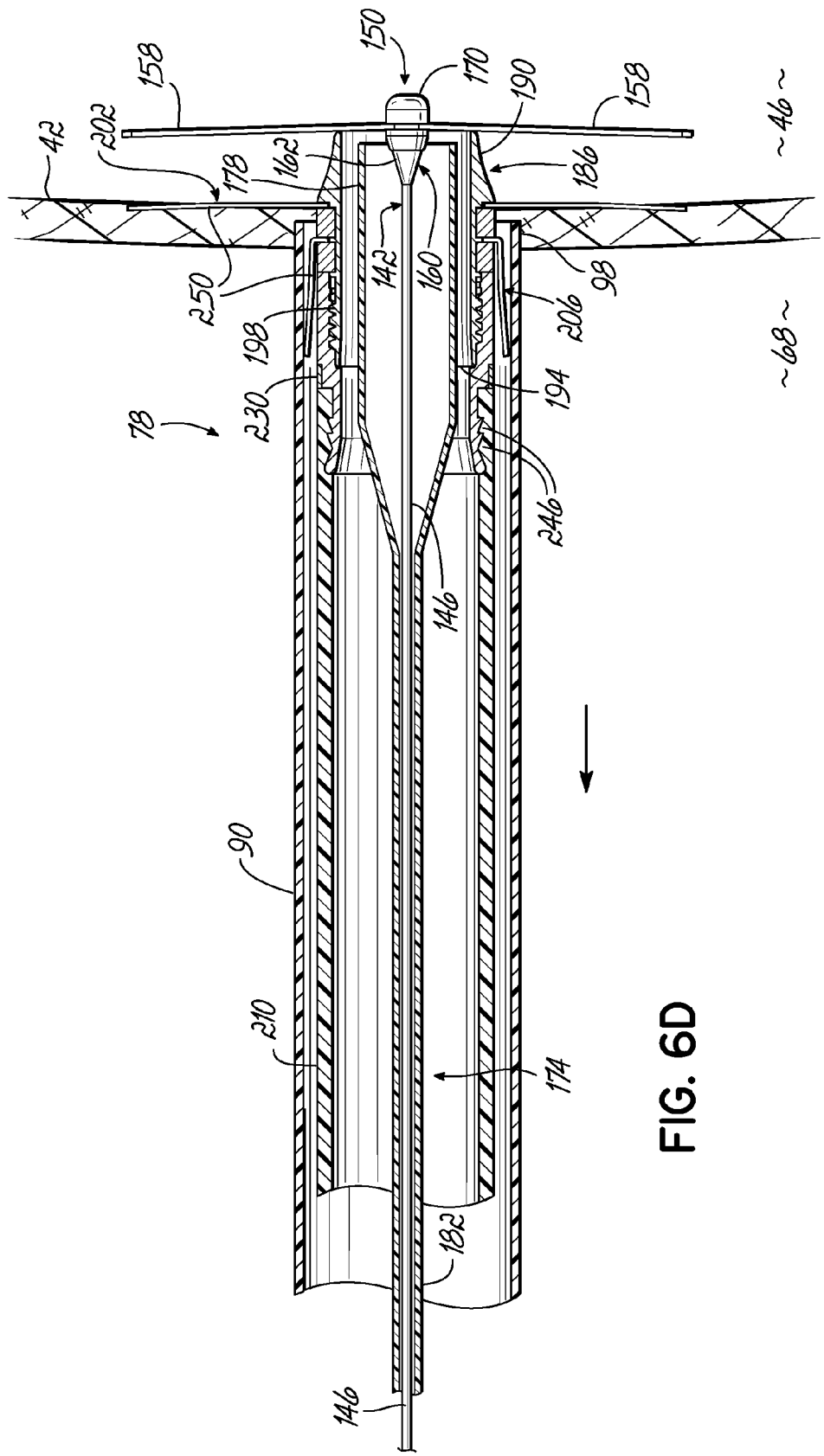

Once proper deployment of the plurality of struts 158 is confirmed, the anchoring guide-element 142 and the delivery catheter 210 with the transseptal tip 186 are retracted until the plurality of struts 158 contacts the distal end 190 of the transseptal tip 186 and the first anchor 202 contacts the intra-atrial septum 42 within the left atrium 46, as shown in FIG. 6D. The delivery device 174 for the anchoring guide-element 142 can now be fully retracted.

Figure 6E:
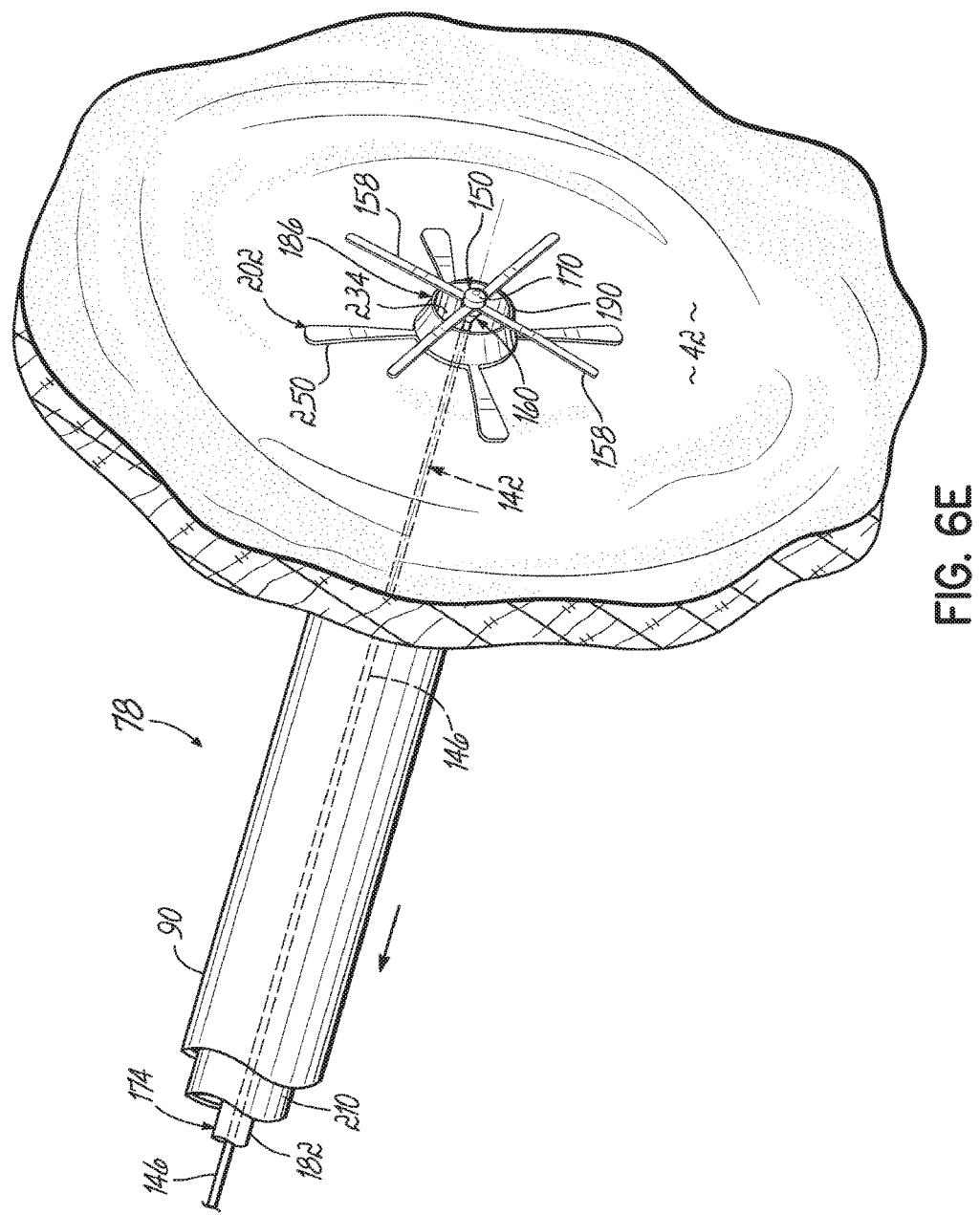
FIG. 6E is a perspective view of the deployed first anchor of the transseptal tip and the deployed plurality of struts of the anchoring guide-element within the left atrium.

FIG. 6E illustrates the deployed first anchor 202 and the deployed plurality of struts 158 with respect to the intra-atrial septum 42.

Figure 6F:
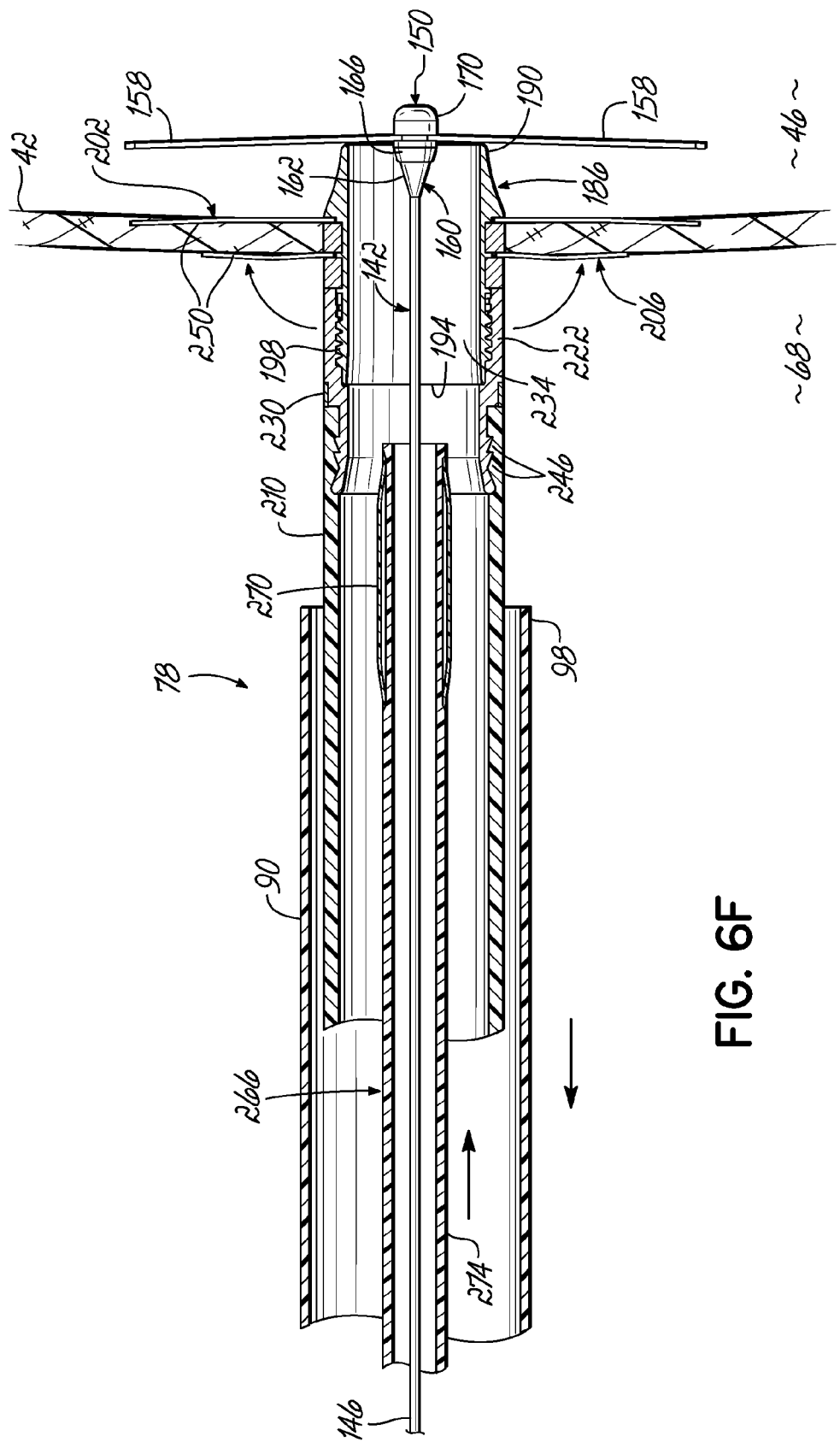
FIG. 6F is a diagrammatic view of an exemplary method of deploying a second anchor of the transseptal tip within the right atrium, shown in cross-section.
Figure 6G:
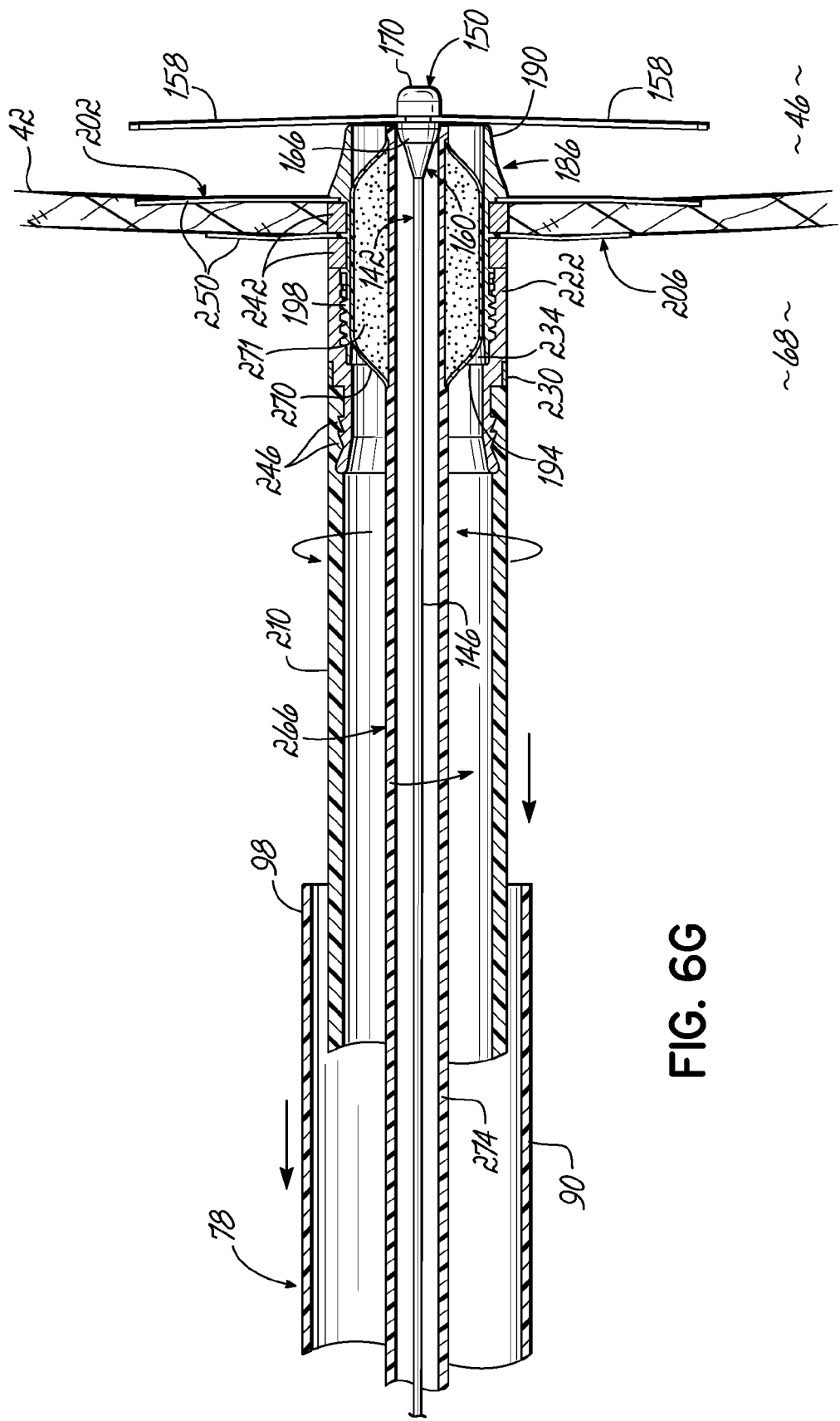
FIGS. 6G-6H are diagrammatic views of an exemplary method of removing and retracting the delivery catheter from the transseptal tip, shown in cross-section.

To deploy the second anchor 206, as shown in FIG. 6F, the physician advances a deflated balloon catheter 266 into the lumen of the delivery catheter 210. The balloon 270 of the suitable balloon catheter 266 can be constructed of a compliant to non-compliant material, including Nylon-11, Nylon-12, polyurethane, polybutylene terephthalate (PBT), PEBAX, or polyethylene terephthalate (PET). The balloon 270 is then coupled to the distal portion of a catheter shaft 274, which can be constructed of the same or a different material as the balloon 270. Coupling of the balloon 270 to the catheter shaft 274 can be by thermal bonding, adhesives, solvent, or covalent bonding. A radiopaque marker (not shown) can be included upon the distal end of the catheter shaft 274 for providing in vivo localization and alignment of the balloon 270 within the lumen 234 of the transseptal tip 186.

Once the balloon 270 of the balloon catheter 266 is within the lumen 234 of the transseptal tip 186, an inflation fluid 271 is used to inflate the balloon 270 until it contacts the inner diameter of the transseptal tip 186. This contact may be used to stabilize the position of the transseptal tip 186 during the deployment of the second anchor 206.

To deploy the second anchor 206, the delivery sheath 78 is retracted once again, while the positions of the transseptal tip 186 (via the delivery catheter 210 and the inflated balloon catheter 266) and the anchoring guide-element 142 are maintained. This retraction can be aided by the in vivo visualization of the marker 98 on the delivery sheath 78. After sufficient retraction, the second anchor 206 is deployed and engages the intra-atrial septum 42 within the right atrium 68. The physician can then confirm that the second anchor 206 is fully deployed by in vivo visualization of a radiopaque marker (not shown) on the plurality of struts 250 of the second anchor 206.

Figure 6H:
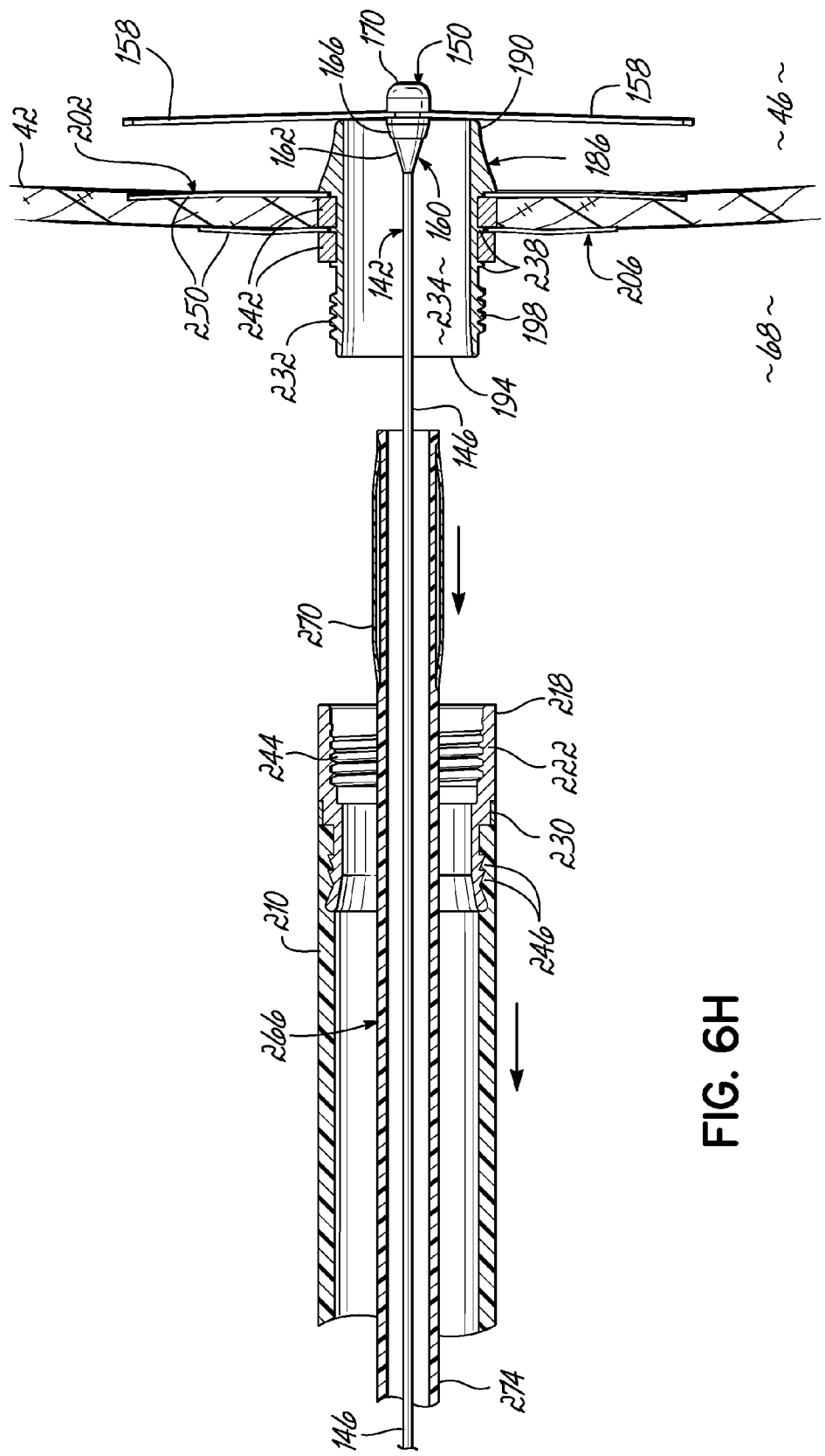

After confirming that the second anchor 206 is fully deployed and the delivery sheath 78 is fully retracted, the delivery catheter 210 can be removed from the transseptal tip 186. To remove the delivery catheter 210, as shown in FIG. 6H, the balloon catheter 266 remains in contact with the inner surface of the transseptal tip 186 while the delivery catheter 210 is uncoupled from the transseptal tip 186 and fully retracted. The balloon catheter 266 is then deflated and retracted as well.

As noted above, the use of the primary incision site 10 (FIG. 1) is useful for gaining direct access to the intra-atrial septum 42 (FIG. 1) and for applying the force necessary to introduce the transseptal tip 186 (FIG. 5A) to the intra-atrial septum 42 (FIG. 1). However, the remainder of the surgical procedure is preferably accomplished from a secondary incision site 24 (FIG. 1). The secondary incision site 24 (FIG. 1) allows the physician to use a shorter length of flexible cannula body than if the primary incision site 10 (FIG. 1) had been used; however, the method should not be considered so limited. The snare device 66 (FIG. 1) is utilized to transition, or move, the operation procedure from the primary incision site 10 (FIG. 1) to the secondary incision site 24 (FIG. 1).

Figure 6I:
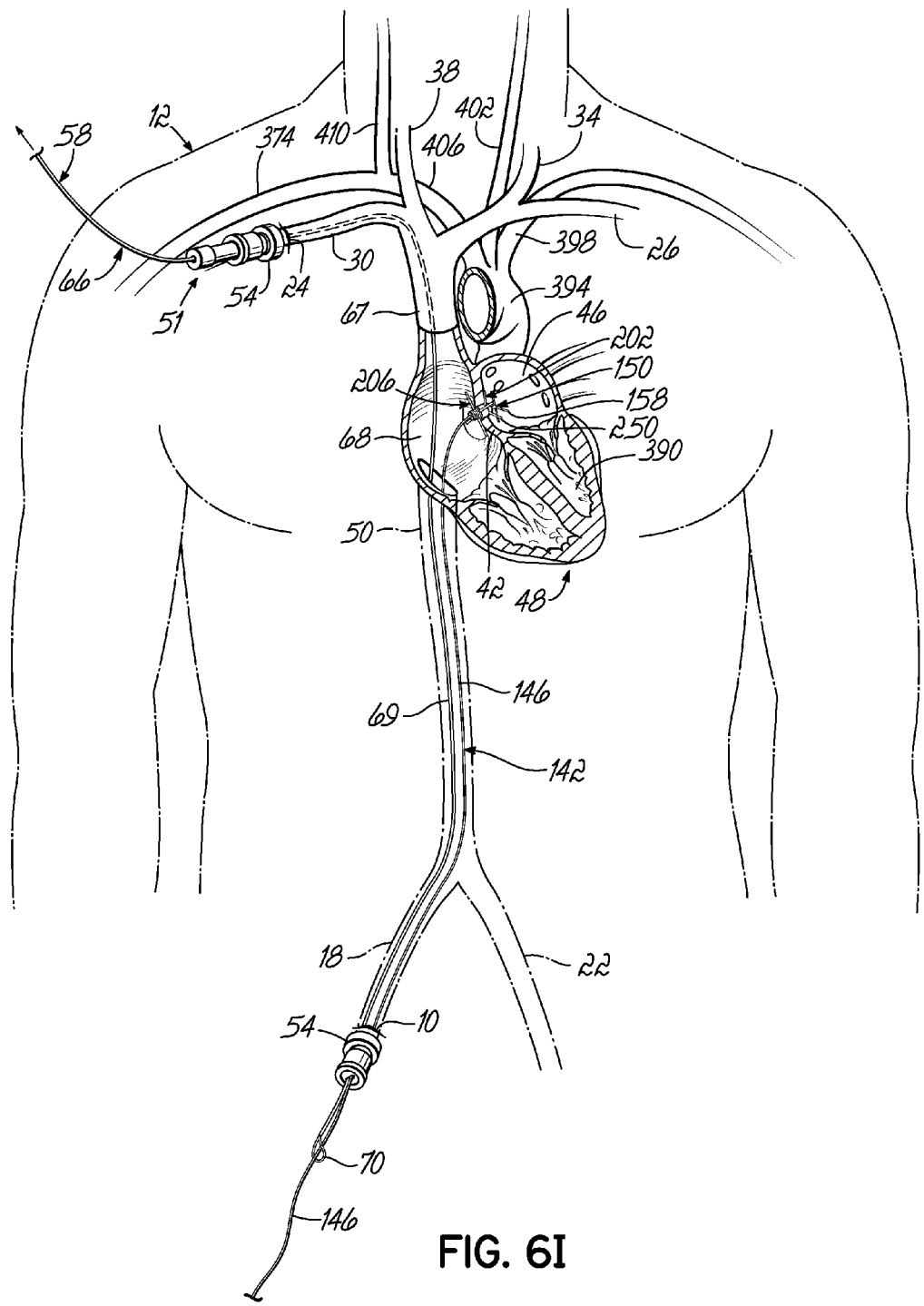
FIGS. 6I-6K are diagrammatic views of an exemplary method of transitioning the anchoring guide-element from a primary incision site to a secondary incision site, shown in cross-section.

FIG. 6I illustrates the body portion 146 of the anchoring guide-element 142 extending through the snare loop 70 after the delivery sheath 78 (FIG. 6H) and the balloon catheter 266 (FIG. 6H) have been retracted from the primary incision site 10.

Figure 6J:
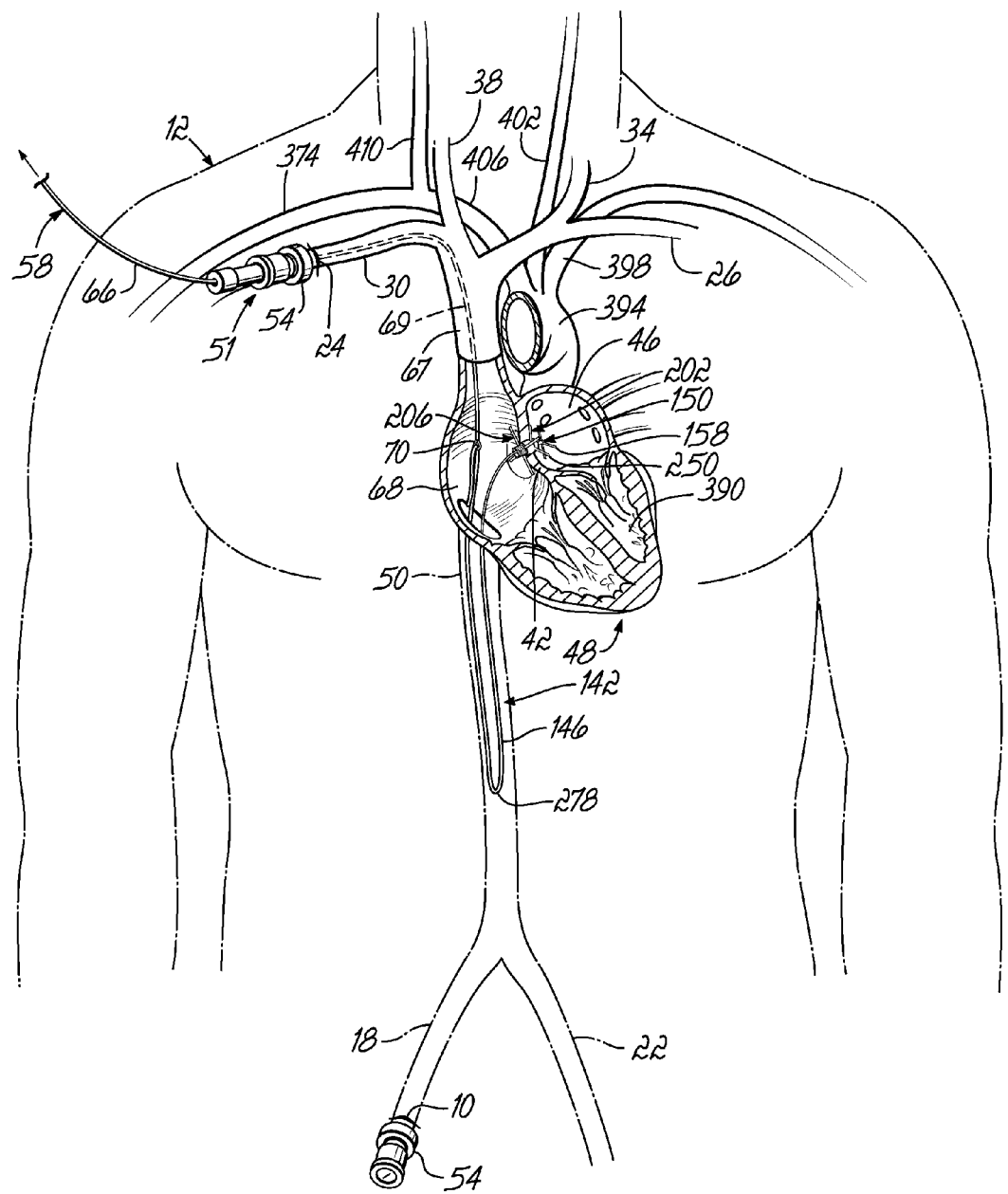
Figure 6K:
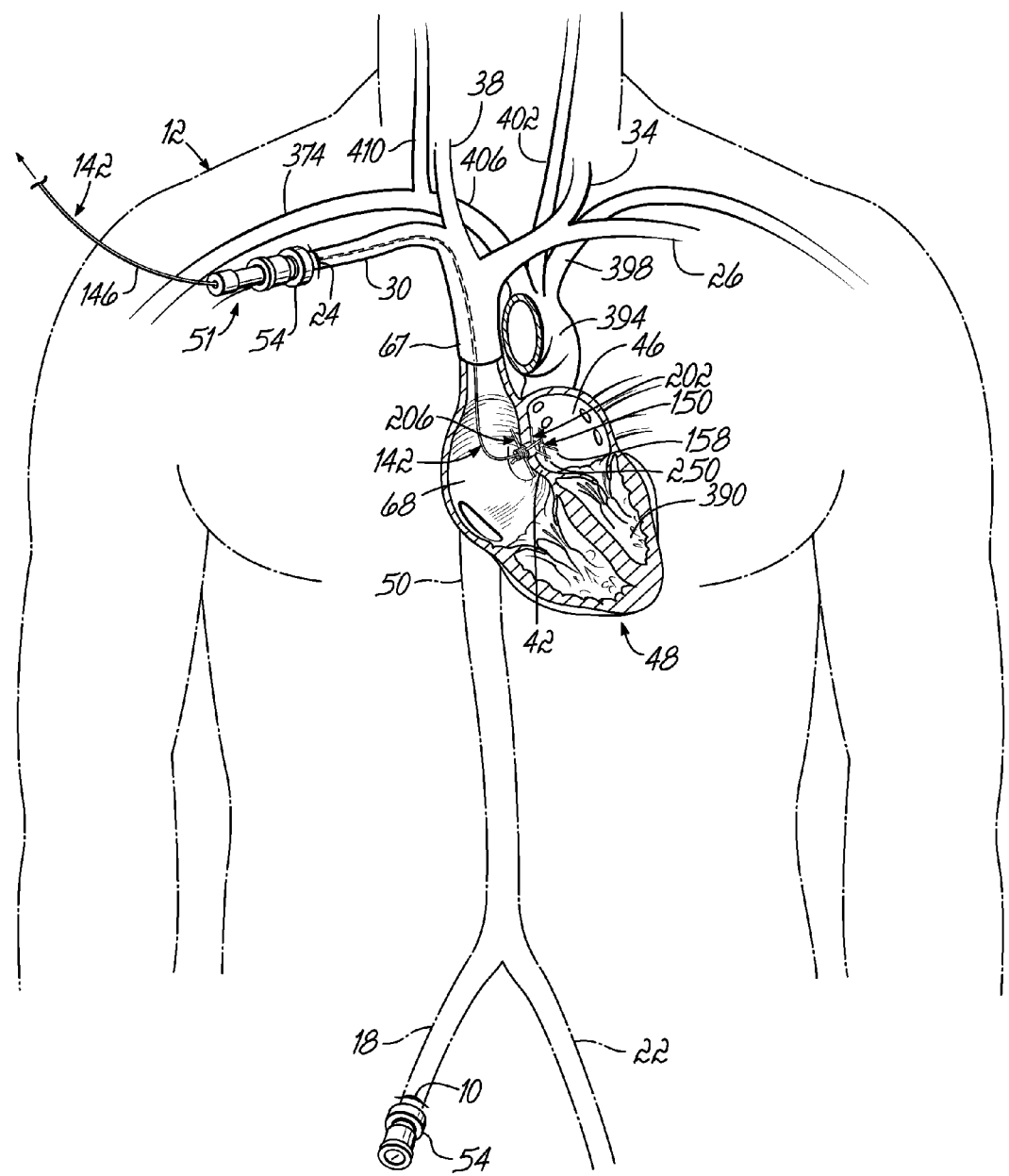

FIG. 6J shows the snare device 66 as the physician begins retracting the body 69 of the snare device 66 and transitioning from the primary incision site 10 to the secondary incision site 24. Because the plurality of struts 158 are secured at the intra-atrial septum 42 within the left atrium 46, the plurality of struts 158 will resist the removal of the anchoring guide-element 142 from the intra-atrial septum 42. By retracting the snare device 66, a prolapsed portion 278 of the body portion 146 is formed. After continued retraction of the snare device 66, the proximal end of the body portion 146 extends through the secondary incision site 24, as shown in FIG. 6K.

In some embodiments, such as those disclosed in U.S. patent application Ser. No. 12/256,911, the proximal end of the body portion 146 could remain extended through the primary incision site 10 while a medial section of the body portion 146 extends externally from the secondary incision site 24. This embodiment can prevent an inadvertent application of too much force to the anchoring portion 150, thereby causing the anchoring portion 150 to pull through the intra-atrial septum 42.

With the body portion 146 of the anchoring guide-element 142 extending from the secondary incision site 24, the method of advancing the flexible cannula body can continue with reference to FIGS. 6L-6R. However, before the flexible cannula body can be directed into the secondary incision site 24, the dilator 53 (FIG. 6K) and the introducer set 61 (FIG. 6K) are removed from the hub 54 of the introducer 52 extending from the secondary incision site 24 in a manner that is similar to the methods described above.

Figure 6L:
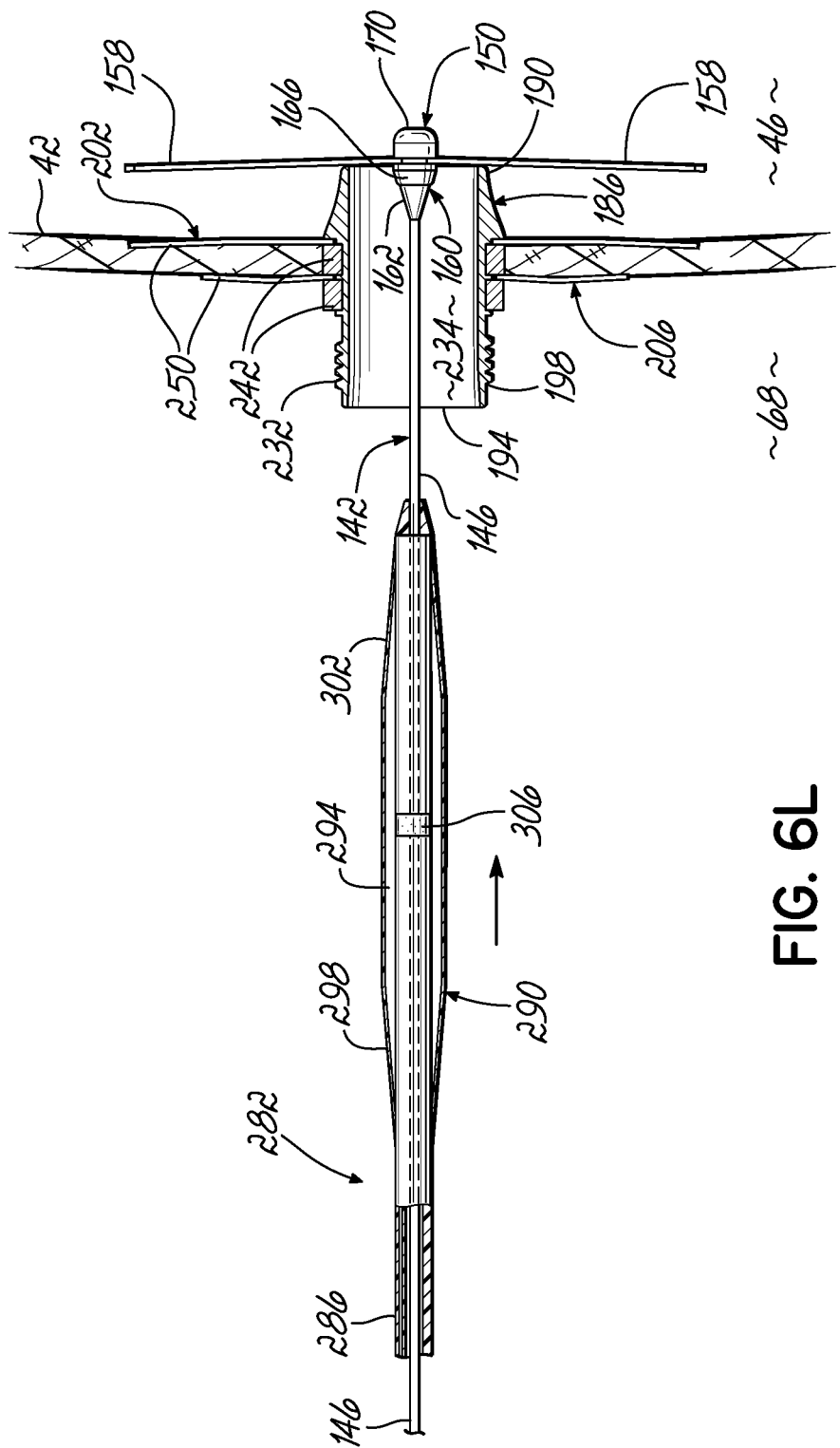
FIG. 6L is a diagrammatic view of an exemplary method of advancing a cannula guide to the transseptal tip, shown in cross-section.
Figure 60:
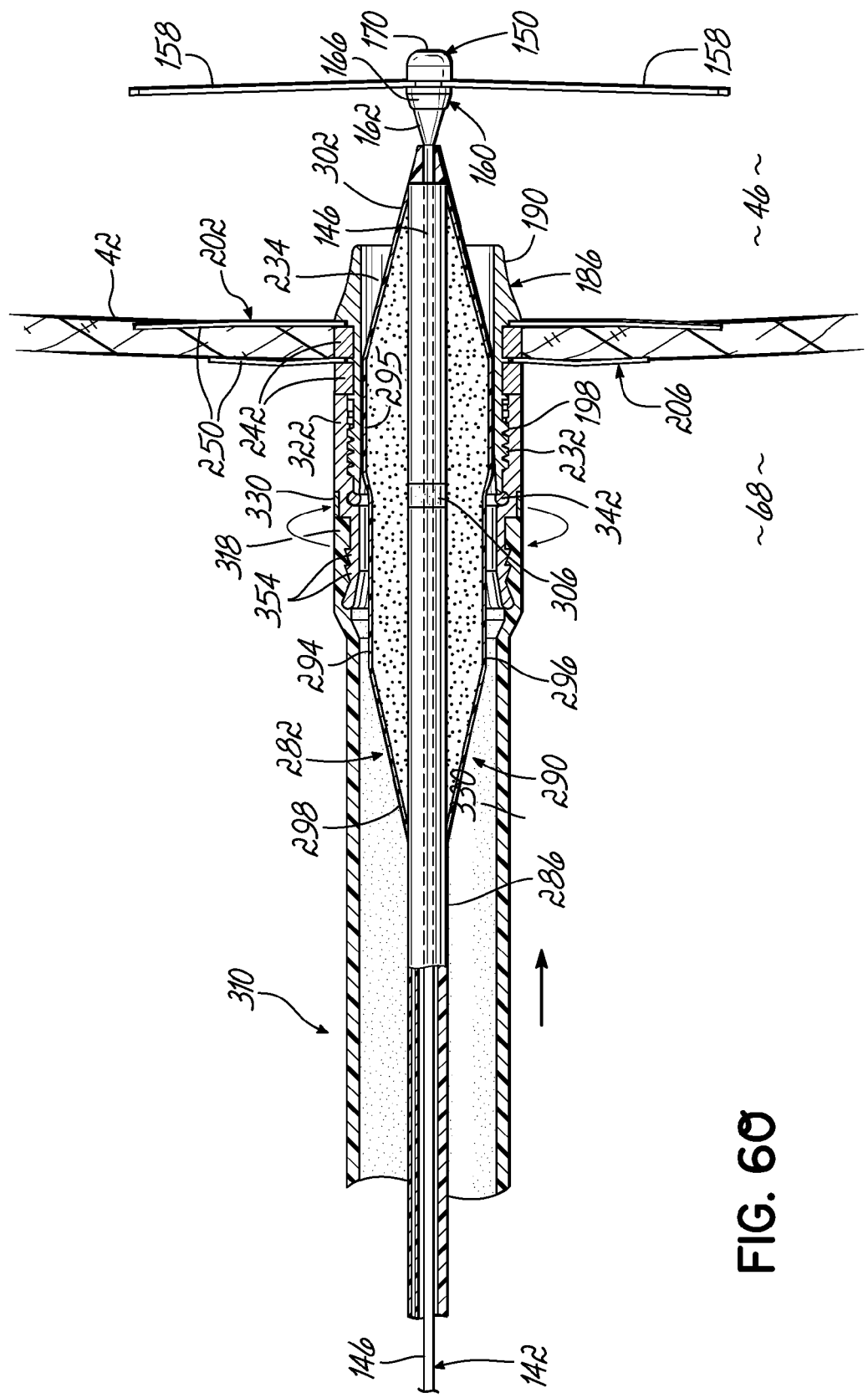

FIG. 6L illustrates the advancement of a cannula guide 282 to the transseptal tip 186, which can be used to align the flexible cannula body (described below) with the transseptal tip 186. The cannula guide 282 includes a body 286 and a expandable member 290 having an alignment section 294, a proximal taper 298, and a distal taper 302. The expandable member 290 can be made from a polymeric material and is injection molded or blow molded onto the body 286; however, it is possible to construct the body 286 and the expandable member 290 separately and adhere the components by a chemical adhesion process. The distal taper 302 is constructed to allow the cannula guide 282 to enter the previously implanted transseptal tip 186 while the proximal taper 298 is constructed to guide the flexible cannula body onto the alignment section 294 in a manner that is described in detail below.

The body 286 can be an extruded polymeric material with a marker 306 positioned within the alignment section 294 to indicate the center of the alignment section 294 once assembled. The marker 306 may be constructed from a metallic material, such as gold (Au) or platinum (Pt) or from a polymeric material embedded with a dense powder, such as tungsten (W).

The cannula guide 282 can then be back-loaded over the anchoring guide-wire 142 and advanced to the transseptal tip 186, as shown in FIG. 6L. In some embodiments, it may be preferred for the flexible cannula body (described below) to be back-loaded with the cannula guide 282, as a unit, over the anchoring guide-element 142. As the cannula guide 282 is slowly advanced, the distal taper 302 enters the transseptal tip 186. Yet further advancement causes the alignment section 294 to enter the lumen 234 of the transseptal tip 186.

With the cannula guide 282 advanced to the transseptal tip 186, the transseptal tip 186 is ready to receive the flexible cannula body 310. FIG. 6M illustrates the flexible cannula body 310, which includes a proximal end 314 and a distal end 318 having a receiving portion 322. The walls of the flexible cannula body 310 are preferably constructed from a biodurable, low durometer thermoplastic or thermoset elastomer material. Specifically, this can include an extruded aliphatic, polycarbonate base polyurethane; aliphatic polyether polyurethane; aromatic polyether polyurethane; aromatic polycarbonate based polyurethane; silicone modified polyurethane, thermoplastic elastomers, copolymers, or blends of urethanes; or silicone that will conform to the tortuosity of the vasculature in which it will reside. At least a portion of the flexible cannula body 310 can further include a reinforcing member that provides support and to minimize the chance of kinking. The reinforcing member may be a metallic coil 326 or braid (not shown) to enhance the torque response of the flexible cannula body 310. As described previously with the delivery catheter 210 (FIG. 5A), to further increase the torque response, the coil 326 can be constructed to wind in a direction that is similar to the direction of rotation used to engage the receiving portion 322 to the engaging portion 198 (FIG. 6N). The reinforcing member will typically terminate prior to the distal and proximal ends 318, 314 of the flexible cannula body 310 so that the distal and proximal ends 318, 314 are not reinforced and remain pliable.

Antimicrobial agents can be embedded within the flexible cannula body material prior to the forming process to effectively reduce or eliminate the presence of bio-film and reduce the potential for infection. Alternatively, the antimicrobial agent may be applied to the surface of the flexible cannula body 310 after the molding process is complete.

In some embodiments, a lubricious coating or layer can be included on the exterior of the flexible cannula body 310. Such a lubricious layer would aid in the movement of the flexible cannula body 310 with respect to the vascular network. Suitable materials for the layer would include etched polytetrafluorethylene (ePTFE), fluorinated ethylene propylene (FEP), ethylene vinyl acetate (EVA), polyvinylidene difluoride (PVDF), high density polyethylene (HDPE), PEBAX, or polyamide materials coated with a lubricious coating similar to HYDROMED.

Once the flexible cannula body 310 is properly formed, it is cut to the desired length. The pliable proximal end 314 can be flared for coupling the flexible cannula body 310 to a pump (described below) of the circulatory assist device. Alternatively, the proximal end 314 can be formed to be about twice the thickness of the remainder of the flexible cannula body 310, which can also assist in coupling the flexible cannula body 310 to the pump of the circulatory assist device.

The pliable distal end 318 of the flexible cannula body 310 may also be flared for receiving the engaging portion 198 in a manner that is described in greater detail below.

The flexible cannula body 310 can include a marker 330 sufficiently near the receiving portion 322 and made from a dense metal, such as gold (Au) or platinum (Pt), for providing in vivo localization of the receiving portion 322.

Turning now to FIG. 6N illustrating the flexible cannula body with greater detail, the receiving portion 322 can include an internal seal ring 342 within a ring groove 346.

The seal ring 342, once assembled with the engaging portion 198, will allow blood flow to transition smoothly from the transseptal tip 186 to the flexible cannula body 310, as described in greater detail below. This smooth blood flow also minimizes the potential for thrombus formation between the transseptal tip 186 and the flexible cannula body 310. A lumen transition 350 can also be provided to further minimize the potential from thrombus formation.

The receiving portion 322 can be coupled to the flexible cannula body 310 by any of a variety of means, including mechanical lock, melt flow, or adhesive bonding. By way of example, the mechanical lock can be barbs 354 or other external features that enhance the securement force between the transseptal tip 186 and the flexible cannula body 310.

With the details of the flexible cannula body 310 described, the method of coupling the flexible cannula body 310 to the transseptal tip 186 continues with reference to FIG. 6N. FIG. 6N illustrates the cannula guide 282 fully inserted within the lumen 234 of the transseptal tip 186 such that the marker 306 aligns with the proximal end 194 of the transseptal tip 186. The expandable member 290 is then inflated such that an outer diameter of a distal portion 295 of the alignment section 294 engages the inner diameter of the transseptal tip 186. The expandable member 290, as shown, can be stepped such that a proximal portion 296 of the alignment section 294 is expandable to a diameter that is slightly less than a diameter of the distal portion 295. This configuration allows the distal portion 295 to contact the inner diameter of the transseptal tip 186 while maintaining a smaller profile proximal portion 296 that will allow the flexible cannula body 310 to slide over the cannula guide 282 and couple to the transseptal tip 186. FIG. 6N also illustrates that in some embodiments, it is permissible for the distal taper 302 of the cannula guide 282 to extend beyond the distal end 190 of the transseptal tip 186 and advance the anchoring portion 150 of the anchoring guide-element 142 slightly distally from the transseptal tip 186; however, this is not required.

With the catheter guide 282 positioned within the transseptal tip 186, the physician can advance the receiving portion 322 of the flexible cannula body 310 to the engaging portion 198 within the right atrium 68. The receiving portion 322 has a tapered thread 334 that matches the thread 232 of the engaging portion 198 of the transseptal tip 186, described previously. The thread 334 can be a low profile, highly polished, coarse female thread 334 that prevents cross threading during engagement of the receiving portion 322 with the engaging portion 198 of the transseptal tip 186. A lead-in 338 to the receiving portion 322 can be tapered to allow for alignment of the transseptal tip 186 and the receiving portion 322. The receiving portion 322 can be a radiopaque material, a polished metallic material (such as titanium (Ti)), or a molded polymeric material (such as nylon) that is compounded using radiopaque filler (for example tantalum (Ta)). In some embodiments, the receiving portion 322 can be coated with a material to prevent thrombus growth.

FIG. 6O illustrates the attaching of the flexible cannula body 310 to the transseptal tip 186. The receiving portion 322 initially engages the proximal taper 298 of the cannula guide 282. With further advancement, the receiving portion 322 engages the alignment section 294 and eventually the transseptal tip 186. Then, while the position of the transseptal tip 186 is maintained by the cannula guide 282, the receiving portion 322 of the flexible cannula body 310 threadably engages the engaging portion 198 of the transseptal tip 186 until the marker 330 of the flexible cannula body 310 is aligned with the marker 306 of the cannula guide 282. This alignment of the markers 306, 330 ensures full engagement and seating of the receiving portion 322 onto the engaging portion 198. With full engagement, two seals are created: an external seal and an internal seal. The external seal is formed between the receiving portion 322 and the most proximal clamp 242. The internal seal is formed between the engaging portion 198 and the seal ring 342.

Although it is not specifically shown, the inner diameter of the transseptal tip 186 can be large enough that an embodiment of the flexible cannula body 310 traverses the lumen of the transseptal tip 186 and is attached to the distal end 190 of the transseptal tip 186 within the left atrium 46. Appropriate attachment means can include screw threads as described above, magnets, adhesives, or other known means. The attachment can be strengthened by including a porous polymeric material, such as the porous polymeric structure 252 (FIG. 5C) described previously with the first and second anchors 202, 206 (FIG. 5C).

Figure 6P:
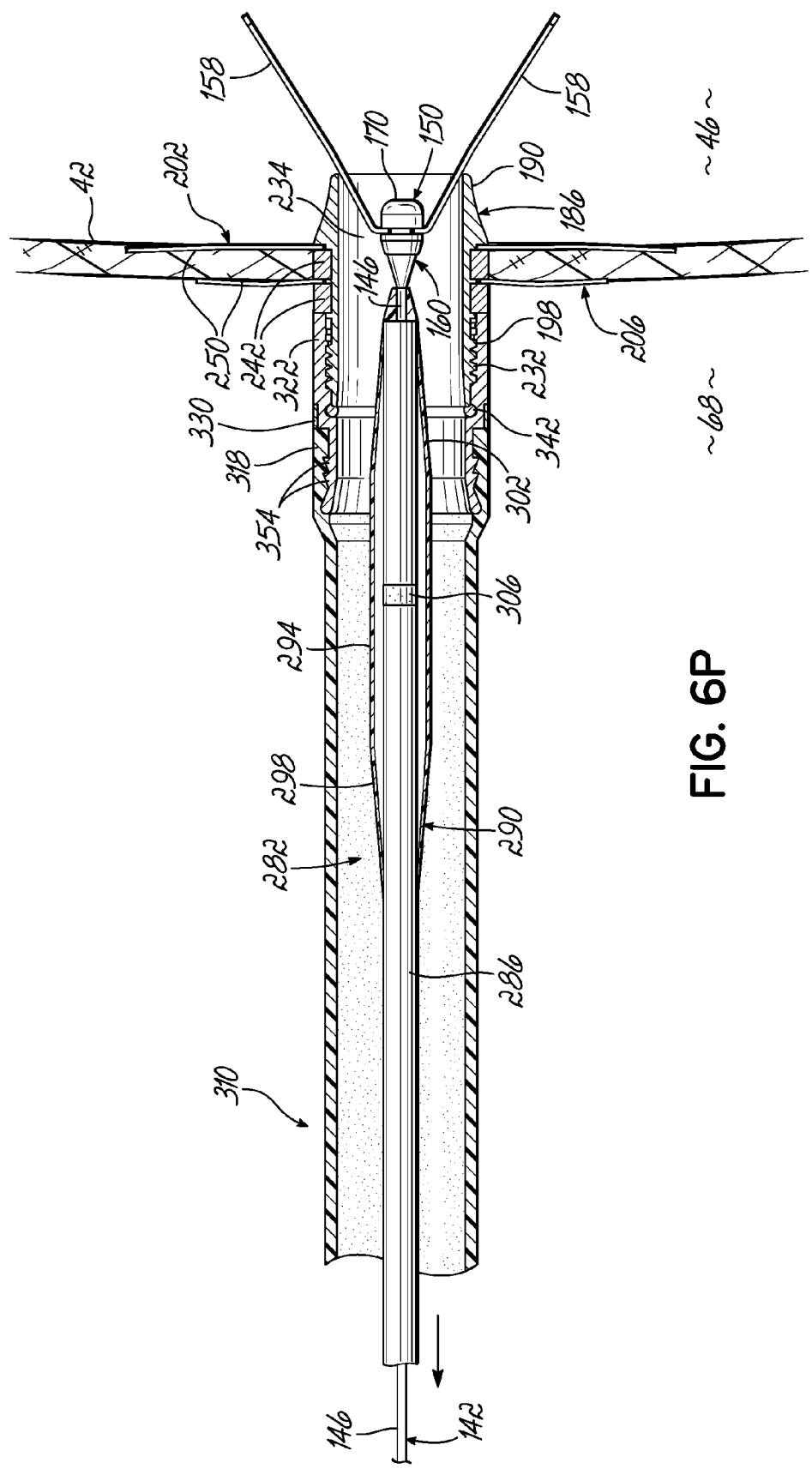
FIG. 6P is a diagrammatic view of an exemplary method of removing the cannula guide and anchoring guide-element from the transseptal tip, shown in cross-section.
Figure 6Q:
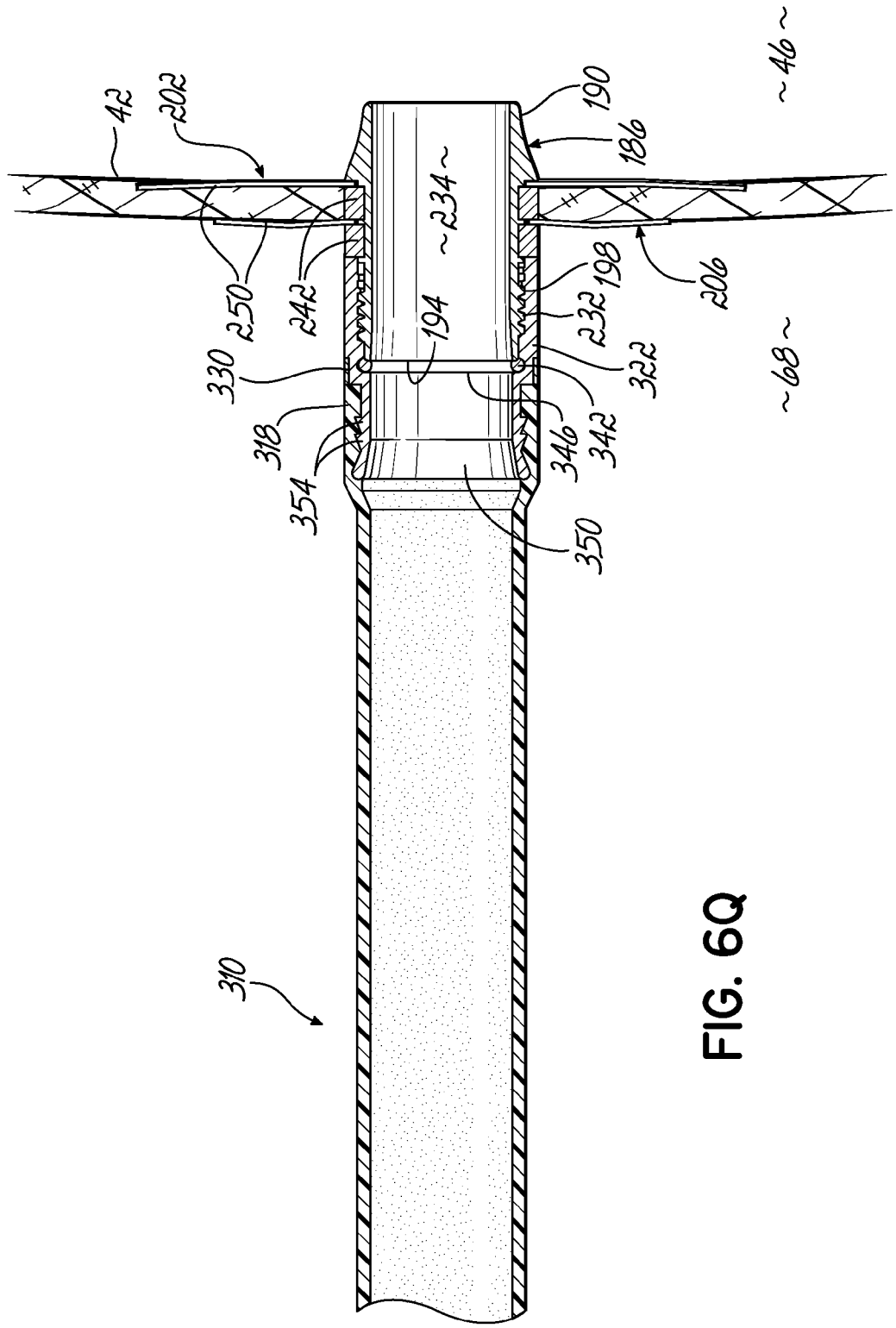
FIG. 6Q is a diagrammatic view of the assembled flexible cannula body and the transseptal tip implanted within the intra-atrial septum, shown in cross-section.

FIG. 6P illustrates the deflation and retraction of the cannula guide 282 as well as the retraction of the anchoring guide-element 142. The anchoring guide-element 142 is removed by maintaining the position of the transseptal tip 186 by the flexible cannula body 310 and retracting the body portion 146 of the anchoring guide-element 142. This retraction movement will force the anchoring portion 150 against the transseptal tip 186, causing the deflection of the plurality of struts 158 into the lumen 234 of the transseptal tip 186. Once the plurality of struts 158 is deflected, the anchoring guide-element 142 is retracted through the lumen of the flexible cannula body 310 and out of the secondary incision site 24 (FIG. 1), leaving the flexible cannula body 310 and transseptal tip 186 implanted, as shown in FIG. 6Q.

Figure 6R:
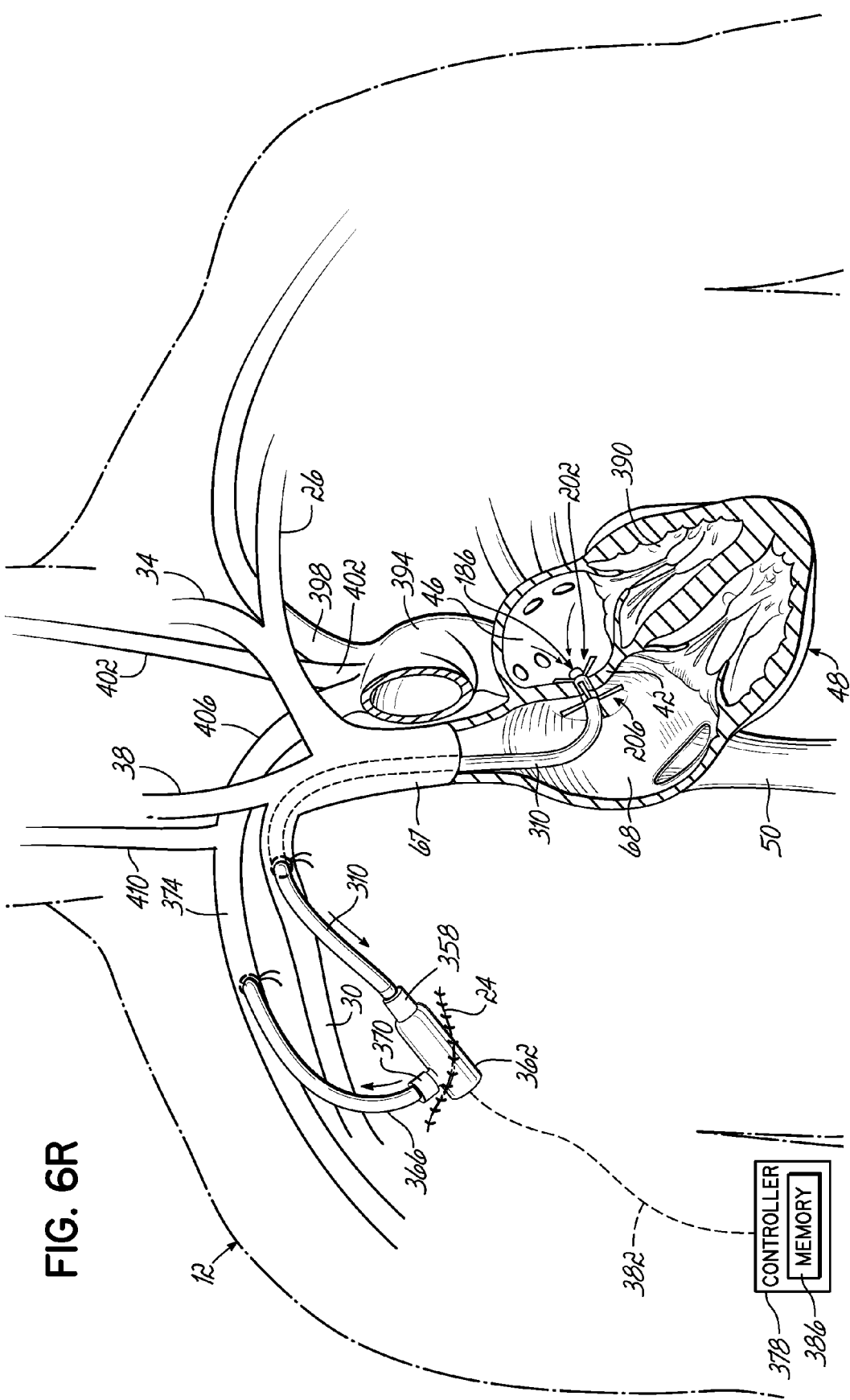
FIG. 6R is a diagrammatic view of an illustrative circulatory assist system positioned in the human heart, shown in cross-section.

FIG. 6R illustrates the implanted transseptal tip 186 and the flexible cannula body 310 as a portion of the circulatory assist system. In that regard, the flexible cannula body 310, which extends from the transseptal tip 186 to the secondary incision site 24 (via the superior vena cava 67 and right subclavian vein 30), is attached to the input port 358 of the implantable pump 362. A separate outflow cannula 366 is attached to an output port 370 of the implantable pump 362, which is then surgically attached so as to communicate with a suitable superficial artery, such as the right subclavian artery 374. At this time, the physician can position the implantable pump 362 subcutaneously or submuscularly within the secondary incision site 24 or maintain the pump 362 externally even after the secondary incision site 24 is closed.

As also shown in FIG. 6R, the pump 362 is operably associated with a controller 378, which can also be implanted or remain external to the patient 12. A signal transmission 382 means is provided between the pump 362 and the controller 378 and can be either a hard-wired or a wireless communications device. In operation, the controller 378 can regulate the pumping action of the pump 362. Additionally, a memory device 386 can be included within the controller 378 that will record pump activity for subsequent physician evaluation and interaction.

The completed flow of blood according to a preferred embodiment and as shown in FIG. 6R will be as follows: oxygenated blood will travel from the left atrium 46 via the natural path into the left ventricle 390 to the aorta 394. From the aorta 394, blood moves into the left subclavian artery 398, the left common carotid 402, and the brachiocephalic trunk 406, which supplies oxygenated blood to the right common carotid 410 and the right subclavian artery 374.

Oxygenated blood will also enter the transseptal tip 186 and flexible cannula body 310 from the left atrium 46. Blood entering the flexible cannula body 310 will travel through the lumen of the flexible cannula body 310 to the implantable pump 362. The implantable pump 362 actively pumps blood into the outflow cannula 366 and into the right subclavian artery 374. From here, the blood is directed into the remainder of the vascular network.

In some patients, there may be a time after the surgery in which the circulatory assist device is no longer necessary. Thus, it would be beneficial to remove the unnecessary components, such as the implantable pump 362 and flexible cannula body 310. Accordingly, one exemplary method of reversing the procedures is illustrated in FIGS. 7A-7G.

Figure 7A:
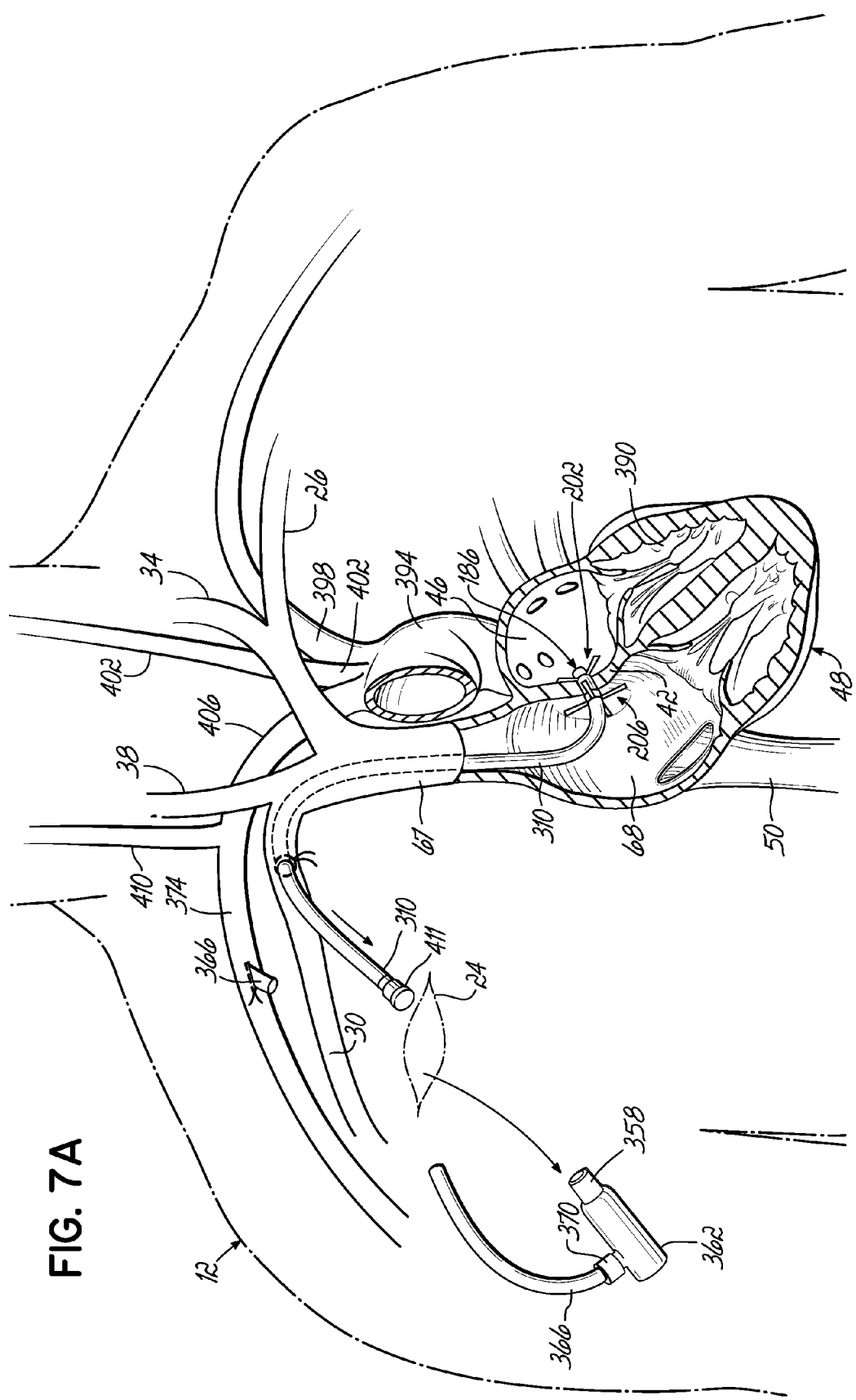
FIGS. 7A-7B are diagrammatic views of an exemplary method of removing the circulatory assist system, shown in cross-section.

The reverse procedure begins, as illustrated in FIG. 7A, with the physician once again creating an incision near the secondary incision site 24. It would be appreciated that while this procedure will be illustrated from the secondary incision site 24, a similar procedure could also be directed from the primary incision site 10 (FIG. 1) or any other appropriate incision site location. It would also be possible for the physician to again use the introducer assembly 51 (FIG. 1A) at the secondary incision site 24, though this is not shown.

With the secondary incision site 24 created, the physician accesses the implantable pump 362 and disconnects the flexible cannula body 310 from the input port 358 of the implantable pump 362. The flexible cannula body 310 is then sealed with a suitable cap 411. The physician then cuts and ligates the outflow cannula 366 near the right subclavian artery 374. The implantable pump 362 with the outflow cannula 366 can then be removed from the secondary incision site 24.

Figure 7B:
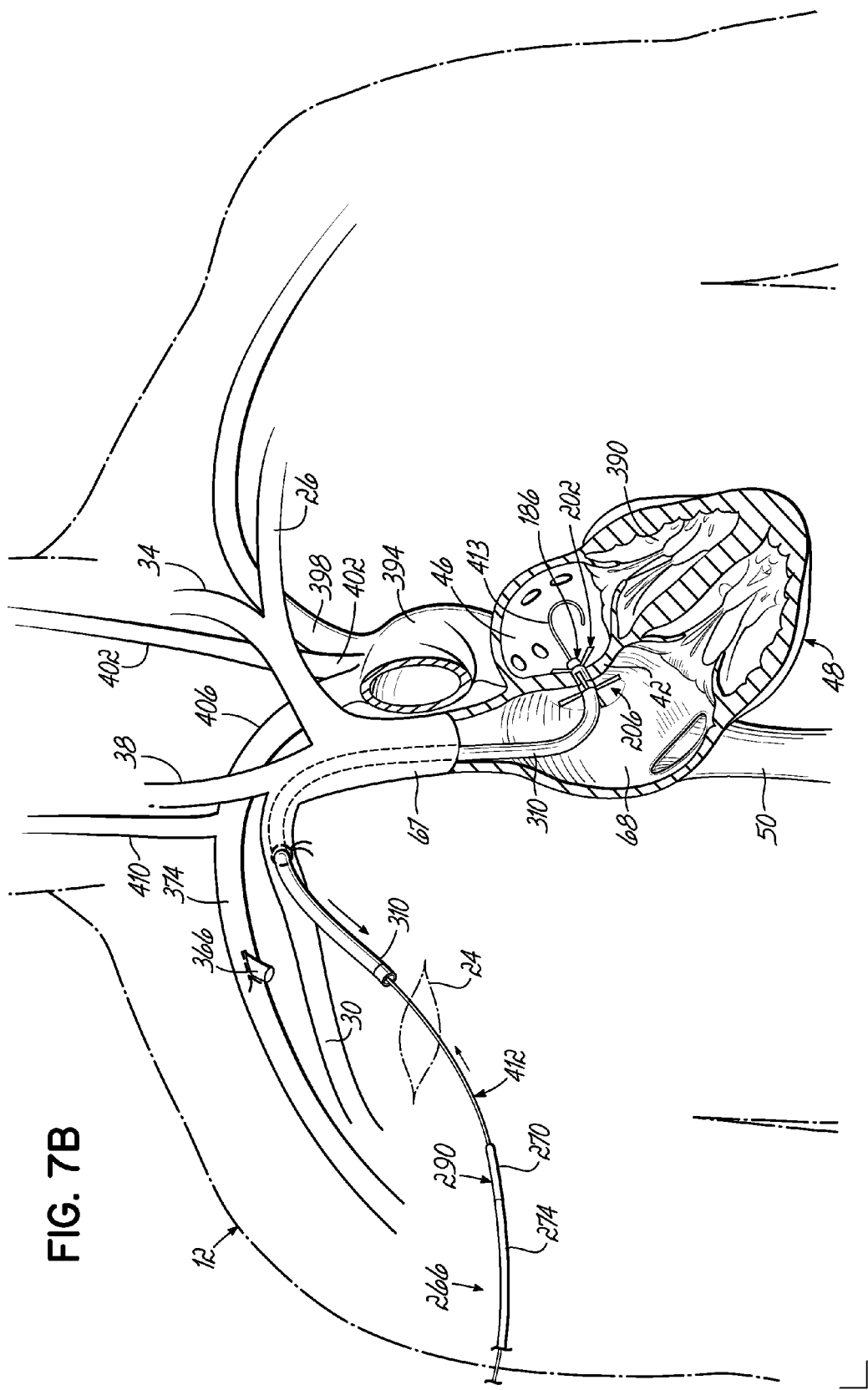

FIG. 7B illustrates the directing of a guide-wire 412 through the lumen of the flexible cannula body 310 and into the left atrium 46. While a standard j-shape 413 guide-wire 412 has been illustrated, it would be understood that other guide-wire shapes, including the anchoring guide-element 142 (FIG. 4A) described above, could also be used. Further, while the procedure has been illustrated with the cap 411 removed, it would be understood that a suitable sealing device capable of permitting passage of the guide-wire 412 could also be used.

FIG. 7B further illustrates the re-advancing of the cannula guide 282 along the guide-wire 412 to the transseptal tip 186.

Figure 7C:
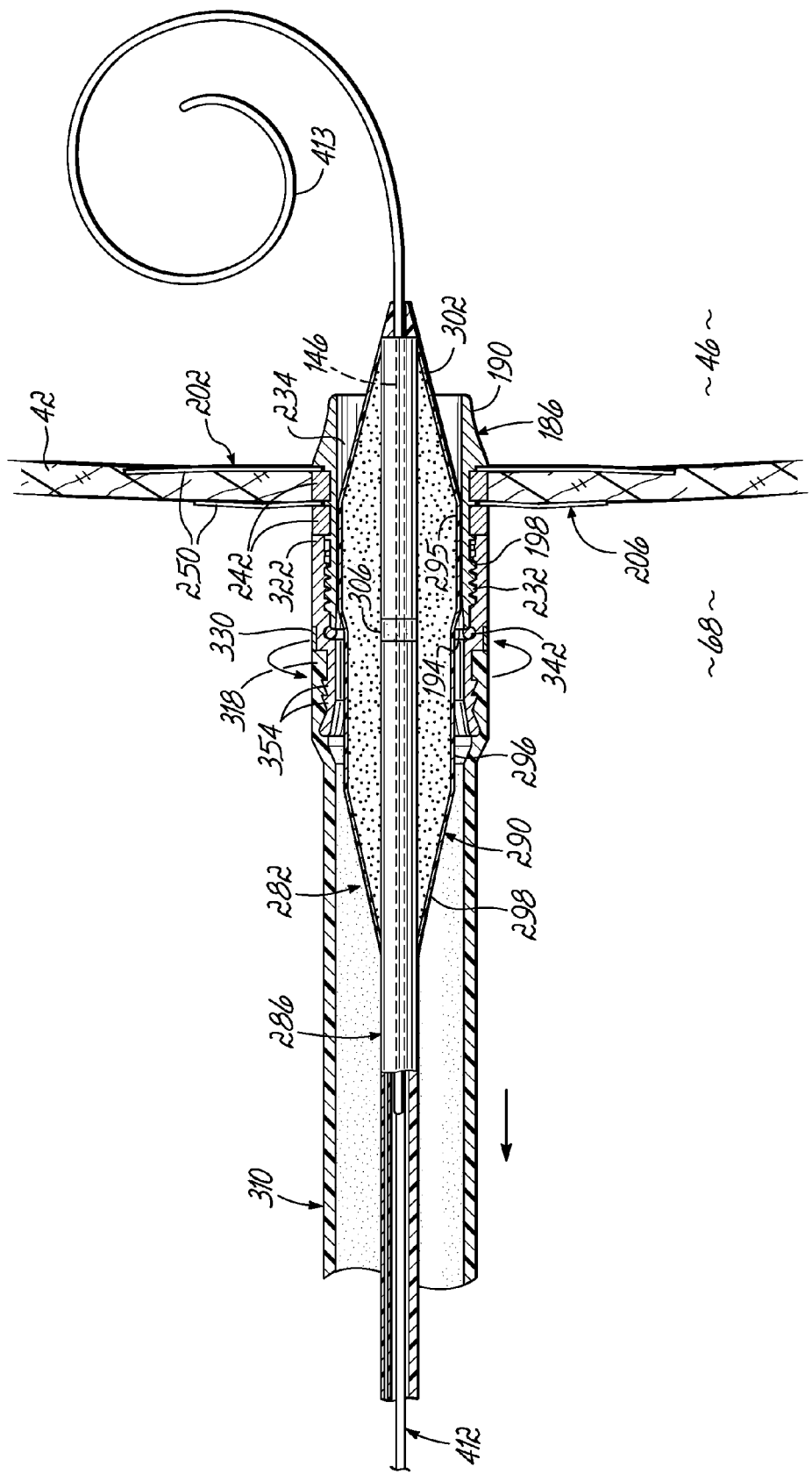
FIGS. 7C-7E are diagrammatic views of an exemplary method of removing the flexible cannula body from the transseptal tip, shown in cross-section.

Once the expandable member 290 is within the transseptal tip 186, as shown in FIG. 7C, it is inflated such that the distal portion 295 of the alignment section 294 contacts the inner diameter of the transseptal tip 186 and secures the position of the transseptal tip 186. The proximal portion 296 is stepped such that the alignment section 294 does not contact an inner surface of the flexible cannula body 310, which also increases the ease of removal. With the position of the transseptal tip 186 secured, the physician can then begin uncoupling the flexible cannula body 310 from the transseptal tip 186. Uncoupling of the flexible cannula body 310 can occur in a manner that is similar to the method described previously for uncoupling the delivery catheter 210 (FIG. 6G) from the transseptal tip 186.

While FIG. 7C illustrates the use of the cannula guide 282 in this exemplary procedure, it would be understood that another balloon catheter or device could be used to stabilize the position of the transseptal tip 186 while the flexible cannula body 310 is removed.

Figure 7D:
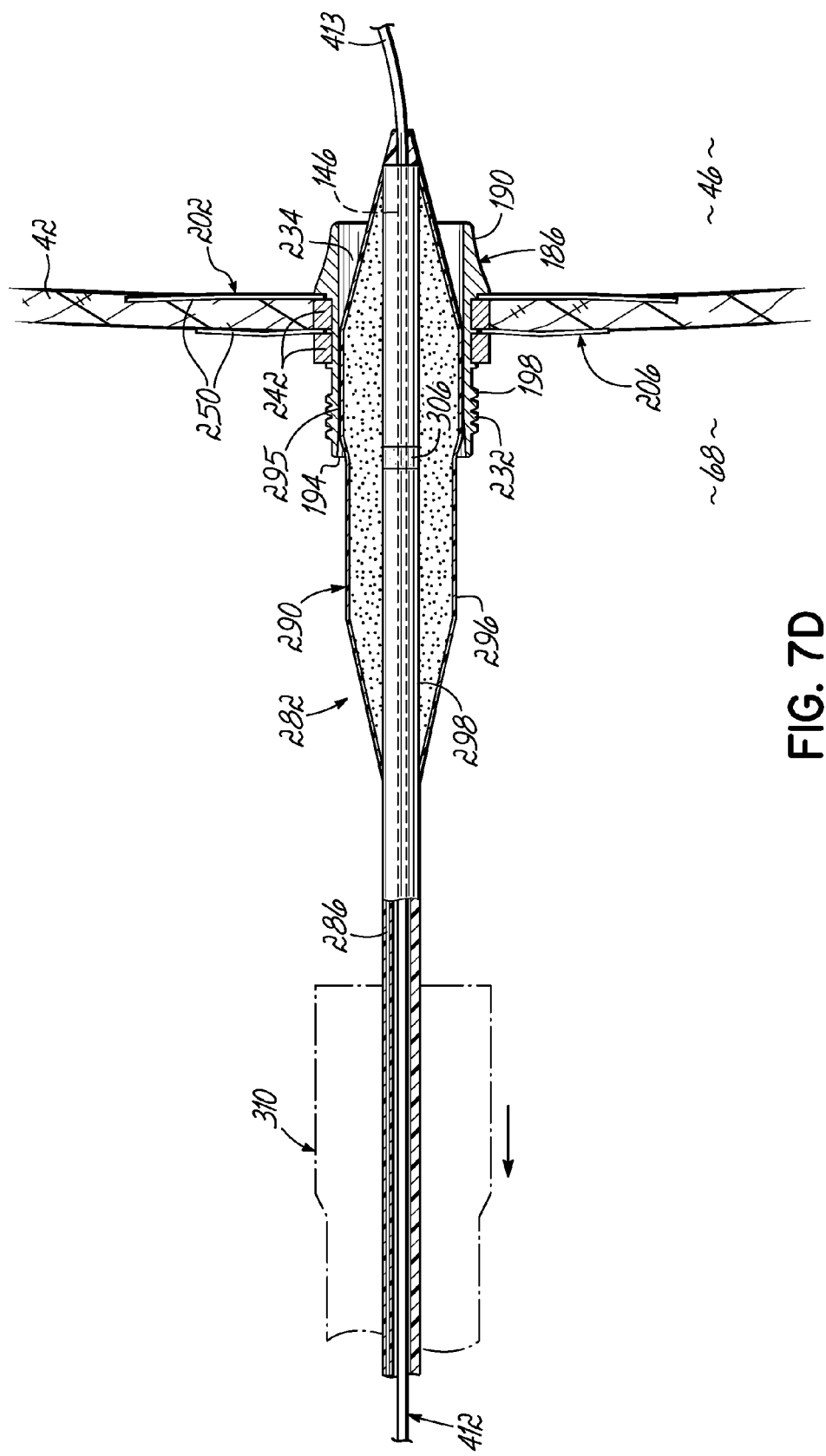

FIG. 7D illustrates the retraction of the flexible cannula body 310 from the transseptal tip 186. Subsequently, the expandable member 290 of the cannula guide 282 is deflated and retracted from the transseptal tip 186, though this step is not specifically shown.

Figure 7E:
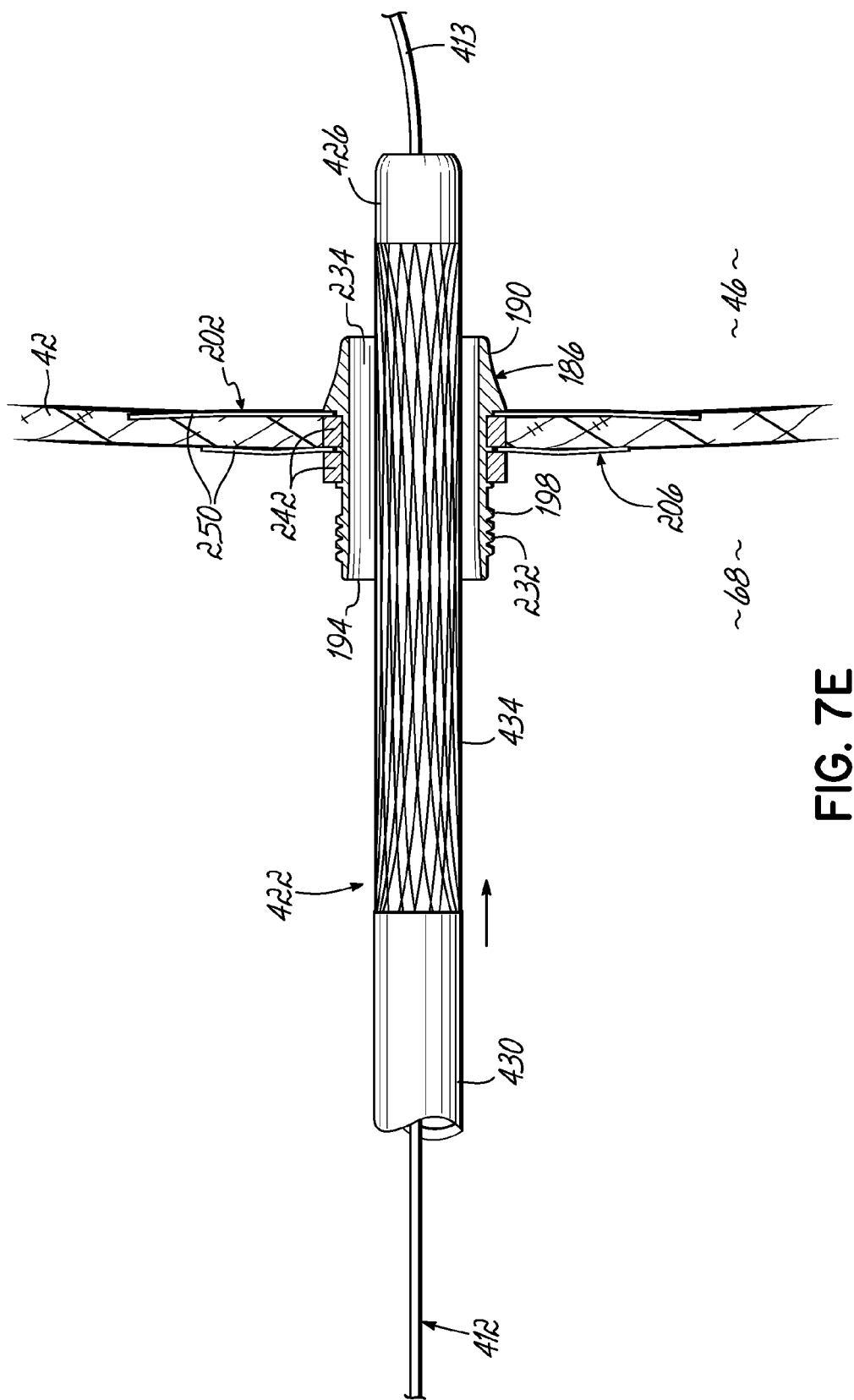

Finally, the present embodiment includes closing off the shunt created between the left and right atriums 46, 68 by the transseptal tip 186. One manner of closing off the shunt is for the physician to direct a closure device 422 over the anchoring guide-element 142 and through the transseptal tip 186, as illustrated in FIG. 7E. Appropriate closure devices 422 can include a distal end 426, a proximal end 430, and a sealing matrix 434 extending therebetween. Suitable commercially available closure devices can include atrial septal defect closure devices, such as the BIOSTAR by NMT Medical, Inc. or the AMPLATZER Septal Occluder by AGA Medical Corp.

FIG. 7F illustrates the release of the closure device 422 such that the sealing matrix 434 expands to form first and second fluid-tight seals 436, 438 at the distal and proximal ends 190, 194, respectively, of the transseptal tip 186. Alternatively as shown in phantom, the first and second fluid-tight seals 440, 442 could extend to include the first and second anchors 202, 206. With the fluid-tight seals 436, 438 in position, the guide-wire 412 and any delivery devices 444 associated with the delivery and/or deployment of the closure device 422 are retracted from the transseptal tip 186 and the secondary incision site 24 (FIG. 7A).

Figure 7G:
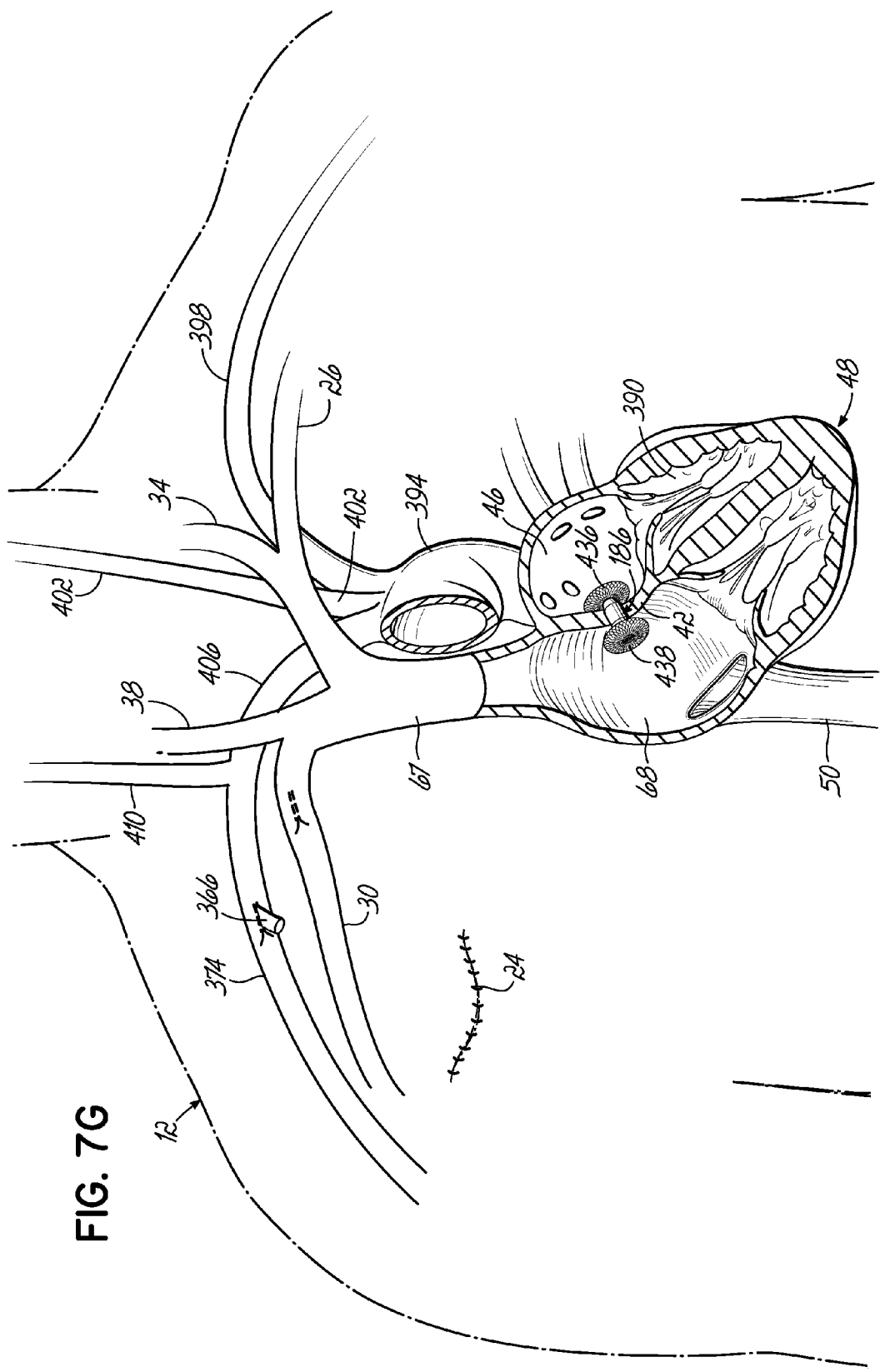
FIG. 7G is a diagrammatic view of the sealed transseptal tip after the flexible cannula body has been removed, shown in cross-section.

With the implantable pump 362 (FIG. 7A) and flexible cannula body 310 (FIG. 7A) removed, the physician sutures the incisions created in the right subclavian vein 30 the secondary incision site 24, as shown in FIG. 7G.

While the present invention has been illustrated by a description of various preferred embodiments and while these embodiments have been described in some detail, it is not the intention of the Applicant to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A cannula assembly, comprising:
   a flexible cannula body having distal and proximal ends with a lumen extending therebetween, the distal end including a receiving portion;
   a rigid transseptal tip having distal and proximal ends, the proximal end including an engaging portion operable to connect to the receiving portion of the flexible cannula body in vivo; and
   first and second anchors coupled to the rigid transseptal tip and configured to be deployed from a contracted state to an expanded state, the first and second anchors configured to engage opposite sides of a heart tissue in the expanded state, and the first and second anchors being located proximate to the engaging portion, the first and second anchors are foldable to a position parallel with a lengthwise central axis of the rigid transseptal tip when in the contracted state and extend to a position transverse to the lengthwise central axis when in the expanded state, the first anchor being distal to and radially offset from the second anchor.

2. The cannula assembly of claim 1, wherein the engaging portion of the transseptal tip has a threaded surface configured to rotatably engage and thereby connect to the receiving portion of the flexible cannula body.

3. The cannula assembly of claim 1, wherein each of the first and second anchors further comprises a plurality of struts.

4. The cannula assembly of claim 3, wherein the plurality of struts are formed from a superelastic material.

5. The cannula assembly of claim 4, wherein the superelastic material is a tubular structure, a wire, or a flat sheet stock.

6. The cannula assembly of claim 3, wherein the plurality of struts of the second anchor further includes a porous polymeric structure.

7. The cannula assembly of claim 3, wherein the plurality of struts of the first anchor further includes a porous polymeric structure.

8. The cannula assembly of claim 1, wherein the receiving portion of the flexible cannula body further includes a seal ring that engages the proximal end of the transseptal tip and forms a fluid-tight seal within the receiving portion.

9. The cannula assembly of claim 1, wherein at least a portion of the flexible cannula body is reinforced with a coil or a braid to increase a torque response of the flexible cannula body.

10. The cannula assembly of claim 9, wherein the distal and proximal ends of the flexible cannula body are not reinforced.

11. A transseptal tip delivery system in combination with the cannula assembly of claim 1, further comprising:
a delivery catheter having distal and proximal ends and a lumen extending therebetween, the distal end including a receiving portion operable to removably disengage the engaging portion of the transseptal tip in vivo; and
a delivery sheath configured to receive the delivery catheter and the transseptal tip and move relative thereto for deploying the first and second anchors into the expanded state.

12. The transseptal tip delivery system of claim 11, wherein the delivery catheter is configured to move the transseptal tip relative to the delivery sheath.

13. The transseptal tip delivery system of claim 11 further comprising:
a balloon catheter configured to engage an inner surface of the transseptal tip and to resist movement of the transseptal tip from the heart tissue while the receiving portion of the delivery sheath is disengaged from the engaging portion of the transseptal tip.

14. The transseptal tip delivery system of claim 11, wherein the delivery catheter is reinforced with a coil or a braid along at least a portion of its length to increase a torque response of the delivery catheter.

15. A cannula guide in combination with the cannula assembly of claim 1, comprising:
an expandable member having distal and proximal tapers and an alignment section therebetween; and a body extending proximally from the expandable member, the expandable member configured to engage an inner surface of the transseptal tip and to resist movement of the transseptal tip from the heart tissue while the receiving portion of the flexible cannula body is connected to the engaging portion of the transseptal tip.

16. The cannula guide of claim 15, wherein the proximal taper is configured to direct the receiving portion of the flexible cannula body to the engaging portion of the transseptal tip.

17. The cannula guide of claim 15, wherein the expandable member includes a distal portion for engaging the inner surface of the transseptal tip and a proximal portion having a diameter that is less than a diameter of the distal portion.

* * * * *